United States Patent
Kadow et al.

(10) Patent No.: US 10,221,156 B2
(45) Date of Patent: Mar. 5, 2019

(54) PYRIDIN-3-YL ACETIC ACID DERIVATIVES AS INHIBITORS OF HUMAN IMMUNODEFICIENCY VIRUS REPLICATION

(71) Applicant: ViiV HEALTHCARE UK (No. 5) LIMITED, Brentford, Middlesex (GB)

(72) Inventors: John F. Kadow, Wallingford, CT (US); B. Narasimhulu Naidu, Wallingford, CT (US); Manoj Patel, Wallingford, CT (US); Prasanna Sivaprakasam, Wallingford, CT (US)

(73) Assignee: VIIV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/579,977

(22) PCT Filed: Jul. 6, 2016

(86) PCT No.: PCT/IB2016/054048
§ 371 (c)(1),
(2) Date: Dec. 6, 2017

(87) PCT Pub. No.: WO2017/006260
PCT Pub. Date: Jan. 12, 2017

(65) Prior Publication Data
US 2018/0162831 A1      Jun. 14, 2018

Related U.S. Application Data

(60) Provisional application No. 62/189,975, filed on Jul. 8, 2015.

(51) Int. Cl.
| | |
|---|---|
| *C07D 401/04* | (2006.01) |
| *C07D 401/14* | (2006.01) |
| *C07D 405/14* | (2006.01) |
| *C07D 413/14* | (2006.01) |
| *C07D 417/14* | (2006.01) |
| *A61P 31/18* | (2006.01) |

(52) U.S. Cl.
CPC ............ *C07D 401/04* (2013.01); *A61P 31/18* (2018.01); *C07D 401/14* (2013.01); *C07D 405/14* (2013.01); *C07D 413/14* (2013.01); *C07D 417/14* (2013.01)

(58) Field of Classification Search
CPC .. C07D 401/04; C07D 401/14; C07D 405/14; C07D 413/14; C07D 417/14; A61P 31/18
USPC ...................................... 514/222.2
See application file for complete search history.

(56) References Cited

U.S. PATENT DOCUMENTS 9,193,720 B2 * 11/2015 Naidu .................. C07D 417/14
2010/0292227 A1 11/2010 Yoakim et al.

FOREIGN PATENT DOCUMENTS

| WO | WO 2013/012649 A1 | 1/2013 |
| WO | WO 2014/164409 A1 | 10/2014 |
| WO | WO 2015/126726 A1 | 8/2015 |

* cited by examiner

*Primary Examiner* — Kristin A Vajda
(74) *Attorney, Agent, or Firm* — Robert H. Brink; Kathryn A. Lutomski; Edward R. Gimmi

(57) ABSTRACT

Disclosed are compounds of Formula I, including pharmaceutically acceptable salts, pharmaceutical compositions comprising the compounds, methods for making the compounds and their use in inhibiting HIV integrase and treating those infected with HIV or AIDS.

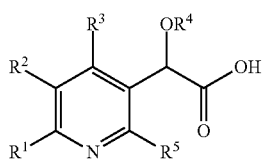

15 Claims, No Drawings

PYRIDIN-3-YL ACETIC ACID DERIVATIVES AS INHIBITORS OF HUMAN IMMUNODEFICIENCY VIRUS REPLICATION

This application is a § 371 of International Application No. PCT/IB2016/054048, filed 6 Jul. 2016, which claims the benefit of U.S. Provisional Application No. 62/189,975, filed 8 Jul. 2015.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2013 point to close to 3.4 million new infections in that year alone. In the same year there were approximately 1.6 million deaths associated with HIV and AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity, i.e., cobicistat, available from Gilead Sciences, Inc. under the tradename TYBOST™ (cobicistat) tablets, has recently been approved for use in combinations with certain antiretroviral agents (ARVs) that may benefit from boosting.

In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See, for example, the following patent applications: WO2007131350, WO2009062285, WO2009062288, WO2009062289, WO2009062308, WO2010130034, WO2010130842, WO2011015641, WO2011076765, WO2012033735, WO2013123148, WO2013134113, WO2014164467, WO2014159959, and WO2015126726.

What is now needed in the art are additional compounds which are novel and useful in the treatment of HIV. Additionally, these compounds may desireably provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

By virtue of the present invention, it is now possible to provide compounds that are novel and are useful in the treatment of HIV. Additionally, the compounds may provide advantages for pharmaceutical uses, for example, with regard to one or more of their mechanism of action, binding, inhibition efficacy, target selectivity, solubility, safety profiles, or bioavailability.

The invention also provides pharmaceutical compositions comprising the compounds of the invention, including pharmaceutically acceptable salts thereof, and a pharmaceutically acceptable carrier, excipient, and/or diluent.

In addition, the invention provides methods of treating HIV infection comprising administering a therapeutically effective amount of the compounds of the invention to a patient.

In addition, the invention provides methods for inhibiting HIV integrase.

Also provided in accordance with the invention are methods for making the compounds of the invention.

The present invention is directed to these, as well as other important ends, hereinafter described.

DESCRIPTION OF THE INVENTION

Unless specified otherwise, these terms have the following meanings.

"Alkyl" means a straight or branched saturated hydrocarbon comprised of 1 to 10 carbons, and preferably 1 to 6 carbons.

"Alkenyl" means a straight or branched alkyl group comprised of 2 to 10 carbons with at least one double bond and optionally substituted with 0-3 halo or alkoxy group.

"Alkynyl" means a straight or branched alkyl group comprised of 2 to 10 carbons, preferably 2 to 6 carbons, containing at least one triple bond and optionally substituted with 0-3 halo or alkoxy group.

"Aryl" mean a carbocyclic group comprised of 1-3 rings that are fused and/or bonded and at least one or a combination of which is aromatic. The non-aromatic carbocyclic portion, where present, will be comprised of $C_3$ to $C_7$ alkyl group. Examples of aromatic groups include, but are not limited to, indanyl, indenyl, naphthyl, phenyl, tetrahydronaphthyl and cyclopropylphenyl. The aryl group can be attached to the parent structure through any substitutable carbon atom in the group.

"Arylalkyl" is a $C_1$-$C_5$ alkyl group attached to 1 to 2 aryl groups and linked to the parent structure through the alkyl moiety. Examples include, but are not limited to, —$(CH_2)_n$Ph with n=1-5, —$CH(CH_3)$Ph, —$CH(Ph)_2$.

"Aryloxy" is an aryl group attached to the parent structure by oxygen.

"Cycloalkyl" means a monocyclic ring system composed of 3 to 7 carbons.

"Halo" includes fluoro, chloro, bromo, and iodo.

"Haloalkyl" and "haloalkoxy" include all halogenated isomers from monohalo to perhalo.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heterocyclyl or heterocyclic" means a cyclic group of 1-3 rings comprised of carbon and at least one other atom selected independently from oxygen, nitrogen and sulfur. The rings could be bridged, fused and/or bonded, through a direct or spiro attachment, with the option to have one or a combination thereof be aromatic. Examples include, but are not limited to, azaindole, azaindoline, azetidine, benzimidazole, bezodioxolyl, benzoisothiazole, benzothiazole, benzothiadiazole, benzothiophene, benzoxazole, carbazole, chroman, dihalobezodioxolyl, dihydrobenzofuran, dihydrobenzo[1,4]oxazine, 1,3-dihydrobenzo[c]thiophene 2,2-dioxide, 2,3-dihydrobenzo[d]isothiazole 1,1-dioxide, 3,4-dihydro-2H-pyrido[3,2-b][1,4]oxazine, 2,3-dihydro-1H-pyrrolo[3,4-c]pyridine and its regioisomeric variants, 6,7-dihydro-5H-pyrrolo[2,3-b]pyrazine and its regioisomeric variants, furanylphenyl, imidazole, imidazo[1,2-a]pyridine, indazole, indole, indoline, isoquinoline, isoquinolinone, isothiazolidine 1,1-dioxide, morpholine, 2-oxa-5-azabicyclo[2.2.1]heptane, oxadiazole-phenyl, oxazole, phenylaztidine, phenylindazole, phenylpiperidine, phenylpiperizine, phenyloxazole, phenylpyrrolidine, piperidine, pyridine, pyridinylphenyl, pyridinylpyrrolidine, pyrimidine, pyrimidinylphenyl, pyrrazole-phenyl, pyrrolidine, pyrrolidin-2-one, 1H-pyrazolo[4,3-c]pyridine and its regioisomeric variants, pyrrole, 5H-pyrrolo[2,3-b]pyrazine, 7H-pyrrolo[2,3-d]pyrimidine and its regioisomeric variants, quinazoline, quinoline, quinoxaline, tetrahydroisoquinoline, 1,2,3,4-tetrahydro-1,8-naphthyridine, tetrahydroquinoline, 4,5,6,7-tetrahydrothieno[3,2-c]pyridine, 1,2,5-thiadiazolidine 1,1-dioxide, thiophene, thiophenylphenyl, triazole, or triazolone. Unless otherwise specifically set forth, the heterocyclic group can be attached to the parent structure through any suitable atom in the group that results in a stable compound.

It is understood that a subset of the noted heterocyclic examples encompass regioisomers. For instance, "azaindole" refers to any of the following regioisomers: 1H-pyrrolo[2,3-b]pyridine, 1H-pyrrolo[2,3-c]pyridine, 1H-pyrrolo[3,2-c]pyridine, and 1H-pyrrolo[3,2-b]pyridine. In addition the "regioisomer variants" notation as in, for example, "5H-pyrrolo[2,3-b]pyrazine and its regioisomeric variants" would also encompass 7H-pyrrolo[2,3-d]pyrimidine, 7H-pyrrolo[2,3-c]pyridazine, 1H-pyrrolo[2,3-d]pyridazine, 5H-pyrrolo[3,2-c]pyridazine, and 5H-pyrrolo[3,2-d]pyrimidine. Similarly, 6,7-dihydro-5H-pyrrolo[2,3-b]pyrazine and its regioisomeric variants would encompass 6,7-dihydro-5H-pyrrolo[2,3-d]pyrimidine and 6,7-dihydro-5H-pyrrolo[2,3-c]pyridazine. It is also understood that the lack of "regioisomeric variants" notation does not in any way restrict the claim scope to the noted example only.

"Heterocyclylalkyl" is a heterocyclyl moiety attached to the parent structure through $C_1$-$C_5$ alkyl group. Examples include, but are not limited to, —$(CH_2)_n$—$R^Z$ or —$CH(CH_3)$—$(R^Z)$ where n=1-5 and that $R^Z$ is chosen from benzimidazole, imidazole, indazole, isooxazole, phenylpyrazole, pyridine, quinoline, thiazole, triazole, triazolone, oxadiazole.

Terms with a hydrocarbon moiety (e.g. alkoxy) include straight and branched isomers for the hydrocarbon portion with the indicated number of carbon atoms.

Bonding and positional bonding relationships are those that are stable as understood by practitioners of organic chemistry.

Parenthetic and multiparenthetic terms are intended to clarify bonding relationships to those skilled in the art. For example, a term such as ((R)alkyl) means an alkyl substituent further substituted with the substituent R.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

"Combination," "coadministration," "concurrent" and similar terms referring to the administration of a compound of Formula I with at least one anti-HIV agent mean that the components are part of a combination antiretroviral therapy or highly active antiretroviral therapy ("HAART") as understood by practitioners in the field of AIDS and HIV infection.

"Therapeutically effective" means the amount of agent required to provide a benefit to a patient as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus.

"Treatment," "therapy," "regimen," "HIV infection," "ARC," "AIDS" and related terms are used as understood by practitioners in the field of AIDS and HIV infection.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

In an aspect of the invention, there is provided a compound of Formula I:

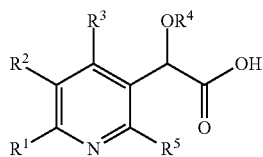

wherein:
$R^1$ is selected from hydrogen or alkyl;
$R^2$ is selected from $(R^6O)$phenyl, $(R^7O)$phenyl or $(R^8O)$phenyl;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, or haloalkoxy;
$R^4$ is selected from alkyl or haloalkyl;
$R^5$ is alkyl;
$R^6$ is $((R^9)(R^{10})N)C_{2-5}$ alkyl;
$R^7$ is selected from alkyl, (cycloalkyl)alkyl, ((alkyl)cycloalkyl)alkyl, cycloalkyl, (alkyl)cycloalkyl, or tetrahydropyranyl, and is further substituted with 0-1 $Ar^1$ substituents;
$R^8$ is selected from indanyl or chromanyl;
$R^9$ is selected from hydrogen or alkyl;
$R^{10}$ is selected from hydrogen or alkyl; or $R^9$ and $R^{10}$ taken together is selected from azetidinyl, pyrrolidinyl, piperidinyl, piperazinyl, morpholinyl, thiomorpholinyl, 1,1-dioxidethiomorpholinyl, homopiperidinyl, homopiperazinyl, or homomorpholinyl, and is substituted with 0-2 alkyl substituents and with 0-1 $Ar^1$ or 0-1 $(Ar^1)C_{1-3}$-alkyl substituents; and
$Ar^1$ is phenyl substituted with 0-3 substituents selected from halo, alkyl, haloalkyl, alkoxy, and haloalkoxy;
or a pharmaceutically acceptable salt thereof.

For a particular compound of Formula I, the scope of any instance of a variable substituent, including $R^1$, $R^2$, $R^3$, $R^4$, $R^5$, $R^6$, $R^7$, $R^8$, $R^9$, $R^{10}$ and $Ar^1$ can be used independently with the scope of any other instance of a variable substituent. As such, the invention includes combinations of the different aspects.

In an aspect of the invention, $R^1$ is alkyl; and $R^3$ is piperidinyl substituted with 0-3 substituents selected from cyano, halo, alkyl, haloalkyl, alkoxy, or haloalkoxy.

In an aspect of the invention, $R^2$ is $(R^6O)$phenyl; and $R^3$ is piperidinyl substituted with 0-3 substituents selected from cyano, halo, alkyl, haloalkyl, alkoxy, or haloalkoxy.

In an aspect of the invention, $R^1$ is alkyl; $R^2$ is $(R^7O)$phenyl; and $R^3$ is piperidinyl substituted with 0-3 substituents selected from cyano, halo, alkyl, haloalkyl, alkoxy, or haloalkoxy.

In an aspect of the invention, $R^1$ is alkyl; $R^2$ is $(R^8O)$phenyl; and $R^3$ is piperidinyl substituted with 0-3 substituents selected from cyano, halo, alkyl, haloalkyl, alkoxy, or haloalkoxy.

In an aspect of the invention, $R^3$ is piperidinyl substituted with 0-3 substituents selected from cyano, halo, alkyl, haloalkyl, alkoxy, or haloalkoxy.

In an aspect of the invention, there is provided a compound of Formula I:

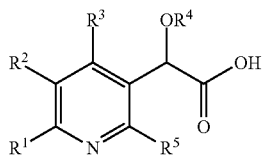

wherein:
$R^1$ is alkyl;
$R^2$ is selected from $(R^6O)$phenyl, $(R^7O)$phenyl or $(R^8O)$phenyl;
$R^3$ is piperidinyl substituted with 0-3 substituents selected from cyano, halo, alkyl, haloalkyl, alkoxy, or haloalkoxy;
$R^4$ is selected from alkyl or haloalkyl;
$R^5$ is alkyl;
$R^6$ is $((R^9)(R^{10})N)C_{2-5}$ alkyl;
$R^7$ is selected from alkyl, (cycloalkyl)alkyl, ((alkyl)cycloalkyl)alkyl, cycloalkyl, (alkyl)cycloalkyl, or tetrahydropyranyl, and is further substituted with 0-1 $Ar^1$ substituents;
$R^8$ is selected from indanyl or chromanyl;
$R^9$ is selected from hydrogen or alkyl;
$R^{10}$ is selected from hydrogen or alkyl;

In an aspect of the invention, $R^2$ is $(R^6O)$phenyl. In an aspect of the invention, $R^2$ is $(R^7O)$phenyl. In an aspect of the invention, $R^2$ is $(R^8O)$phenyl.

In an aspect of the invention, there is provided a composition useful for treating HIV infection comprising a therapeutic amount of a compound of Formula I and a pharmaceutically acceptable carrier. In an aspect of the invention, the composition further comprises a therapeutically effective amount at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier. In an aspect of the invention, the other agent is dolutegravir.

In an aspect of the invention, there is provided a method for treating HIV infection comprising administering a therapeutically effective amount of a compound of Formula I, or a pharmaceutically acceptable salt thereof, to a patient in need thereof. In an aspect of the invention, the method further comprises administering a therapeutically effective amount of at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. In an aspect of the invention, the other agent is dolutegravir. In an aspect of the invention, the other agent is administered to the patient prior to, simultaneously with, or subsequently to the compound of Formula I.

Preferred compounds in accordance with the present invention include the following:

(S)-2-(tert-Butoxy)-2-(4-(4,4-dimethylpiperidin-1-yl)-2,6-dimethyl-5-(4-(2-(4-methylpiperazin-1-yl)ethoxy)phenyl)pyridin-3-yl)acetic acid;

(S)-2-(tert-Butoxy)-2-(5-(4-(2-cyclohexylethoxy)phenyl)-4-(4,4-dimethylpiperidin-1-yl)-2,6-dimethylpyridin-3-yl)acetic acid;

(2S)-2-(tert-Butoxy)-2-(5-(4-(chroman-4-yloxy)phenyl)-4-(4,4-dimethylpiperidin-1-yl)-2,6-dimethylpyridin-3-yl)acetic acid;

(S)-2-(tert-Butoxy)-2-(4-(4,4-dimethylpiperidin-1-yl)-2,6-dimethyl-5-(4-(2-(piperidin-1-yl)ethoxy)phenyl)pyridin-3-yl)acetic acid;

(S)-2-(tert-Butoxy)-2-(4-(4,4-dimethylpiperidin-1-yl)-2,6-dimethyl-5-(4-(2-morpholinoethoxy)phenyl)pyridin-3-yl)acetic acid;

(S)-2-(tert-Butoxy)-2-(4-(4,4-dimethylpiperidin-1-yl)-5-(4-(2-(4-(3-methoxyphenyl)piperidin-1-yl)ethoxy)phenyl)-2,6-dimethylpyridin-3-yl)acetic acid;

(S)-2-(tert-Butoxy)-2-(4-(4,4-dimethylpiperidin-1-yl)-2,6-dimethyl-5-(4-(2-(4-methylpiperidin-1-yl)ethoxy)phenyl)pyridin-3-yl)acetic acid;

(S)-2-(tert-Butoxy)-2-(4-(4,4-dimethylpiperidin-1-yl)-2,6-dimethyl-5-(4-((4-methylcyclohexyl)methoxy)phenyl)pyridin-3-yl)acetic acid;

(S)-2-(tert-Butoxy)-2-(4-(4,4-dimethylpiperidin-1-yl)-5-(4-(2-(4-(4-fluorobenzyl)piperazin-1-yl)ethoxy)phenyl)-2,6-dimethylpyridin-3-yl)acetic acid;

(S)-2-(tert-Butoxy)-2-(4-(4,4-dimethylpiperidin-1-yl)-5-(4-((1-(4-fluorophenyl)cyclopropyl)methoxy)phenyl)-2,6-dimethylpyridin-3-yl)acetic acid;

(S)-2-(tert-Butoxy)-2-(5-(4-((2,3-dihydro-1H-inden-2-yl)oxy)phenyl)-4-(4,4-dimethylpiperidin-1-yl)-2,6-dimethylpyridin-3-yl)acetic acid;

(S)-2-(tert-Butoxy)-2-(4-(4,4-dimethylpiperidin-1-yl)-2,6-dimethyl-5-(4-(2-thiomorpholinoethoxy)phenyl)pyridin-3-yl)acetic acid;

(S)-2-(tert-Butoxy)-2-(4-(4,4-dimethylpiperidin-1-yl)-5-(4-(2-(1,1-dioxidothiomorpholino)ethoxy)phenyl)-2,6-dimethylpyridin-3-yl)acetic acid;

(S)-2-(tert-Butoxy)-2-(4-(4,4-dimethylpiperidin-1-yl)-5-(4-(3-(4-fluorophenyl)cyclobutoxy)phenyl)-2,6-dimethylpyridin-3-yl)acetic acid;

(S)-2-(tert-Butoxy)-2-(4-(4,4-dimethylpiperidin-1-yl)-5-(4-((4-(4-fluorophenyl)cyclohexyl)oxy)phenyl)-2,6-dimethylpyridin-3-yl)acetic acid;

(2S)-2-(tert-butoxy)-2-(4-(4,4-dimethylpiperidin-1-yl)-5-(4-((2-(4-fluorophenyl)cyclopentyl)oxy)phenyl)-2,6-dimethylpyridin-3-yl)acetic acid; and (2S)-2-(tert-Butoxy)-2-(4-(4,4-dimethylpiperidin-1-yl)-5-(4-((4-(4-fluorophenyl)tetrahydrofuran-3-yl)oxy)phenyl)-2,6-dimethylpyridin-3-yl)acetic acid; and pharmaceutically acceptable salts thereof.

The compounds of the invention herein described may typically be administered as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms, including capsules, tablets, lozenges, and powders, as well as liquid suspensions, syrups, elixirs, and solutions. Compositions are made using available formulation techniques, and excipients (such as binding and wetting agents) and vehicles (such as water and alcohols) which are generally used for compositions. See, for example, Remington's Pharmaceutical Sciences, 17th edition, Mack Publishing Company, Easton, Pa. (1985).

Solid compositions which are normally formulated in dosage units and compositions providing from about 1 to 1000 milligram ("mg") of the active ingredient per dose are typical. Some examples of dosages are 1 mg, 10 mg, 100 mg, 250 mg, 500 mg, and 1000 mg. Generally, other antiretroviral agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 milligram per milliliter ("mg/mL"). Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other antiretroviral agents used clinically. Typically, the daily dose will be about 1-100 milligram per kilogram ("mg/kg") body weight daily. Generally, more compound is required orally and less parenterally. The specific dosing regimen, however, will be determined by a physician using sound medical judgment.

The compounds of this invention desireably have activity against HIV. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, HIV capsid inhibitors, anti-infectives, and immunomodulators, such as, for example, PD-1 inhibitors, PD-L1 inhibitors, antibodies, and the like. In these combination methods, the compound of Formula I will generally be given in a daily dose of about 1-100 mg/kg body weight daily in conjunction with other agents. The other agents generally will be given in the amounts used therapeutically. The specific dosing regimen, however, will be determined by a physician using sound medical judgment.

Examples of nucleoside HIV reverse transcriptase inhibitors include abacavir, didanosine, emtricitabine, lamivudine, stavudine, tenofovir, zalcitabine, and zidovudine.

Examples of non-nucleoside HIV reverse transcriptase inhibitors include delavirdine, efavirenz, etrivirine, nevirapine, and rilpivirine.

Examples of HIV protease inhibitors include amprenavir, atazanavir, darunavir, fosamprenavir, indinavir, lopinavir, nelfinavir, ritonavir, saquinavir and, tipranavir.

An example of an HIV fusion inhibitor is enfuvirtide or T-1249.

An example of an HIV entry inhibitor is maraviroc.

Examples of HIV integrase inhibitors include dolutegravir, elvitegravir, or raltegravir.

An example of an HIV attachment inhibitor is fostemsavir.

An example of an HIV maturation inhibitor is BMS-955176, having the following structure:

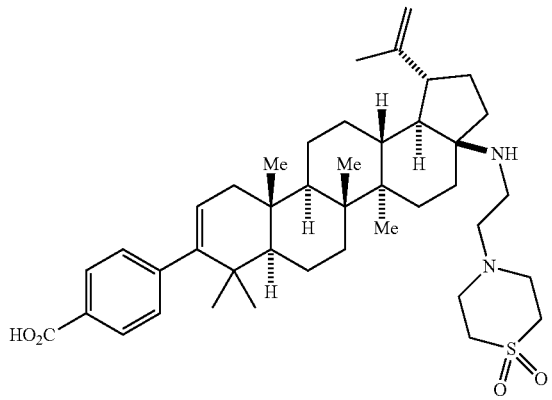

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
| --- | --- | --- |
| ANTIVIRALS | | |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection ARC, PGL |
| AL-721 | Ethigen (Los Angeles, CA) | HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |

-continued

| Drug Name | Manufacturer | Indication |
|---|---|---|
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |

-continued

| Drug Name | Manufacturer | Indication |
| --- | --- | --- |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDs in development |
| CMX-157 Lipid conjugate of nucleotide tenofovir | Chimerix | HIV infection AIDs |
| GSK1349572 Integrase inhibitor TIVICAY ® dolutegravir | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |

-continued

| Drug Name | Manufacturer | Indication |
|---|---|---|
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |

-continued

| Drug Name | Manufacturer | Indication |
|---|---|---|
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Methods of Synthesis

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds of this invention can be prepared by the methods outlined in the Scheme I. Those skilled in the art will recognize, for example, that certain compounds of the invention can be synthesized from an appropriately substituted heterocycle I-1 according to Scheme I. Compounds I-1 and I-6 are commercially available or can be synthesized by reactions well known in the art. Treatment of compound I-1 with bromine provided the dibromo intermediate I-2 which was converted to the chloropyridine I-3 by reacting with POCl$_3$. Intermediate I-3 conveniently transformed to ketoester I-5 using conditions well-known to those skilled in the art, including reacting I-3 with Grignard reagent in the presence of catalytic copper(I) bromide dimethylsulfide complex followed by alkyl 2-chloro-2-oxoacetate. Coupling of amines I-5 with intermediate I-6 in the presence of an organic base such as Hunig's base provided intermediate I-7. Chiral Lewis acid such as I-8 mediated reduction of ketoester I-7 with catecholborane furnished chiral alcohol I-9. Tertiary butylation of alcohol I-9 by well-known conditions, including but not limited to tertiary-butyl acetate and perchloric acid, gave intermediate I-10. Intermediate I-10 conveniently transformed to intermediate I-11 using conditions well-known in the art, including but not limited to the Suzuki coupling between intermediate I-10 and R$^6$B(OR)$_2$. The boronate or boronic acid coupling reagents, well-known in the art, are commercially available or are prepared by reactions well-known to those skilled in the art. Hydrolysis of intermediate I-11 by using conditions well-known to those skilled in the art furnished carboxylic acid I-12.

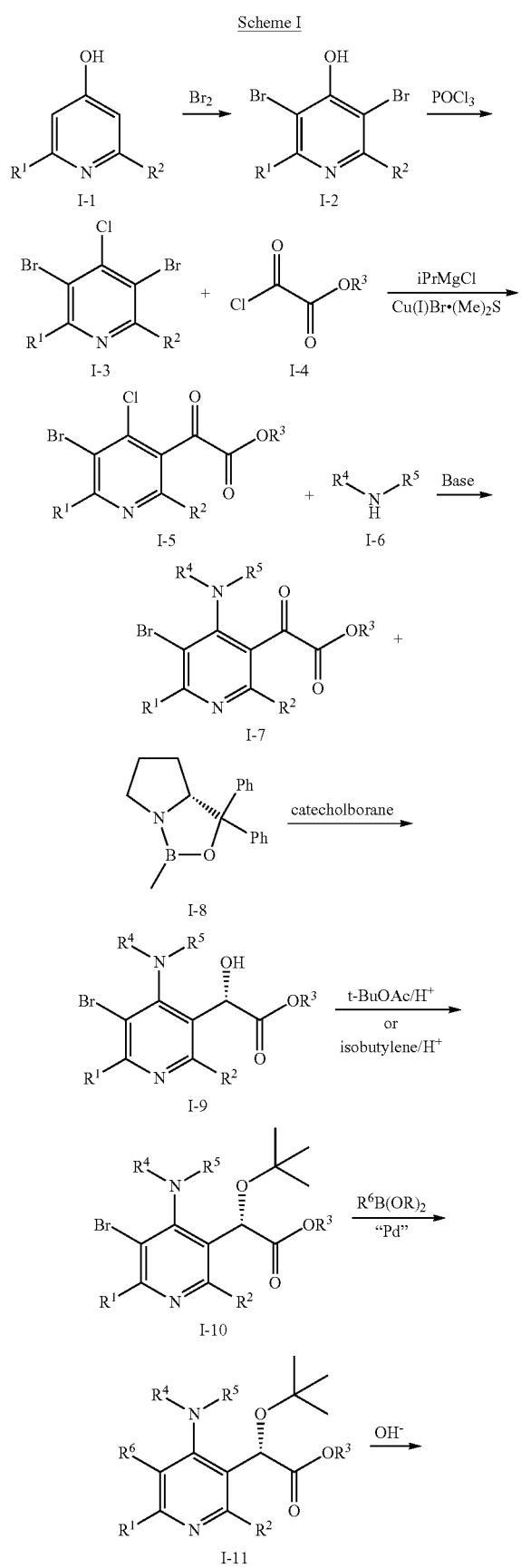

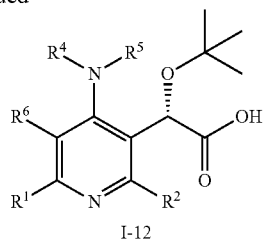

Some compounds of this invention can be prepared by the methods outlined in the Scheme II. Those skilled in the art will recognize, for example, that intermediate I-10 can be conveniently transformed to intermediate II-2 using conditions well-known in the art, including but not limited to the Suzuki coupling between intermediate I-10 and II-1. Cleavage of protecting group in II-2 provided phenol II-3. Alkylation of the phenol II-3 was achieved by using conditions well known to those skilled in the art, including but not limited to Mitshunobu reaction to provide the intermediate II-4. Hydrolysis of intermediate II-4 by using conditions well-known in the literature furnished carboxylic acid II-5.

Scheme II

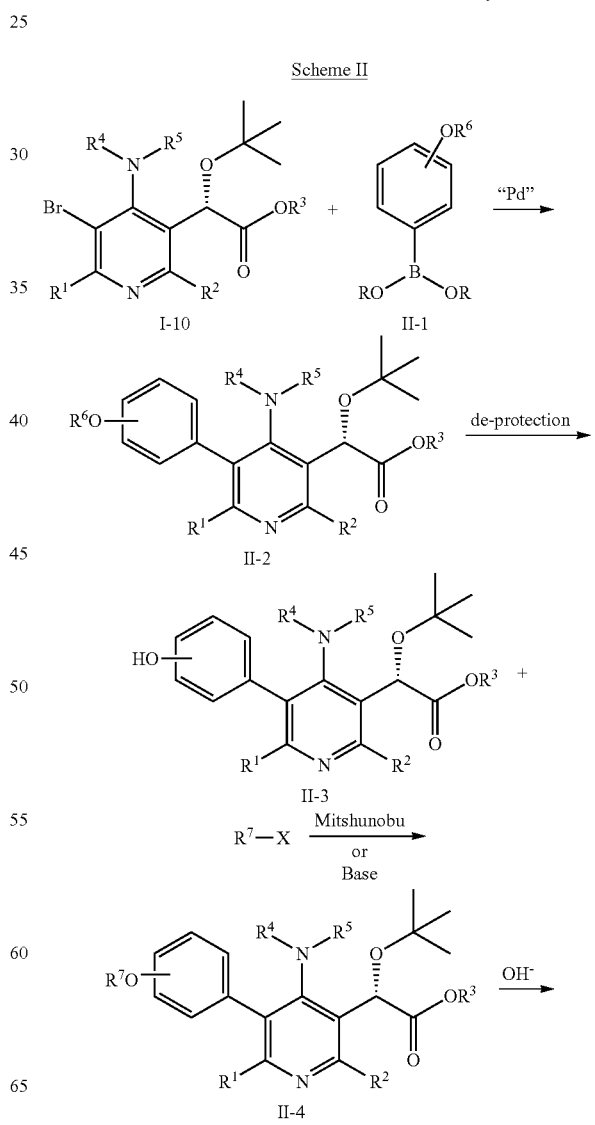

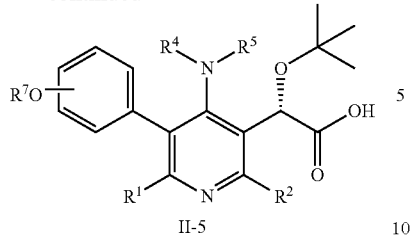

II-5

The compounds described herein were purified by the methods well known to those skilled in art by normal phase column chromatography on silica gel column using appropriate solvent system described. Preparative HPLC purifications mentioned in this experimentation section were carried out gradient elution either on Sunfire Prep C18 ODB column (5 μm; 19 or 30×100 mm) or Waters Xbridge column (5 μM; 19 or 30×100 mm) using the following mobile phases: Mobile phase A: 9:1 H$_2$O/acetonitrile with 10 mM NH$_4$OAc and mobile phase B:A:9:1 acetonitrile/H$_2$O with: 10 mM NH$_4$OAc; or mobile phase A: 9:1 H$_2$O/acetonitrile with 0.1% TFA and mobile phase B:A:9:1 acetonitrile/H$_2$O with: 0.1% TFA; or mobile phase A: water with 20 mM NH$_4$OAc and mobile phase B: 95:5 MeOH/H$_2$O with 20 mM NH$_4$OAc.

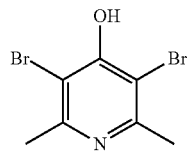

3,5-Dibromo-2,6-dimethylpyridin-4-ol

A 3-neck R.B-flask equipped with mechanical stirrer, addition funnel and condenser is charged with 2,6-dimethylpyridin-4-ol (100 g, 812 mmol), CH$_2$Cl$_2$ (1000 mL) and MeOH (120 mL). To the resulting light brown or tan solution was added tert-BuNH2 (176 ml, 1665 mmol), cooled in water bath maintained between 5-10° C. (ice-water) and added drop wise Br2 (84 ml, 1624 mmol) over 70 min. After the addition was complete cold bath was removed and stirred for 1.5 h at rt. Then, the light orange slurry was filtered and the filter cake was washed with ether (250 mL) and dried to afford 3,5-dibromo-2,6-dimethylpyridin-4-ol, hydrobromide (280.75 g, 776 mmol, 96% yield) as white solid which was used in the next step without further purification. $^1$H NMR (500 MHz, DMSO-d$_6$) δ 12.08 (br. s., 1H), 2.41 (s, 6H). LCMS (M+H)=281.9.

Alternative Procedure:

Bromine (72.8 mL, 1.4 mol) was added via addition funnel over 60 min to a mechanically stirred cold (ice-water bath) solution of 2,6-dimethylpyridin-4-ol (87 g, 706 mmol) and 4-methylmorpholine (156 mL, 1.4 mol) in dichloromethane (1 L) and methanol (100 mL) and then stirred for 2 h at rt. Additional bromine (~15 mL) was added based on monitoring by LCMS. The product was filtered, washed with ether, and dried under vacuum to give 3,5-dibromo-2,6-dimethylpyridin-4-ol 176.8 g (88%).

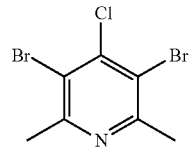

3,5-Dibromo-4-chloro-2,6-dimethylpyridine

Triethylamine (28.8 mL, 206 mmol) was added to a nitrogen purged solution of 3,5-dibromo-2,6-dimethylpyridin-4-ol (58 g, 206 mmol) and phosphorous oxychloride (57.7 mL, 619 mmol) in chloroform (450 mL) and stirred for 1 h at rt, then 3 h at 80° C. The reaction was removed from heating and immediately concentrated under house vaccum; then under high vacuum. The appearance was a cream colored solid, which was azeotroped with toluene (2×100 mL); treated with ice (200 g) for 10 min and carefully neutralized with NaHCO$_3$ (powder), and 1N NaOH solution, and extracted with DCM (2×400 mL). The combined organic layers were dried (MgSO$_4$), concentrated, and a beige solid was obtained that was washed with hexanes and dried under high vacuum to give 3,5-dibromo-4-chloro-2,6-dimethyl-pyridine 52.74 g (85.1%). Concentration of the hexanes gave 3.5 g of less pure product. $^1$H NMR (500 MHz, CDCl$_3$) δ 2.59 (s, 6H). LCMS (M+H)=300.0.

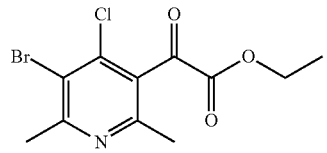 [SMILES: CCOC(=O)C(=O)c1c(C)nc(C)c(Br)c1Cl]

Ethyl 2-(5-bromo-4-chloro-2,6-dimethylpyridin-3-yl)-2-oxoacetate

To a stirred mixture of 3,5-dibromo-4-chloro-2,6-dimethylpyridine (14.94 g, 49.9 mmol) and Cu(I)Br Me2S (0.513 g, 2.495 mmol) in THF (50 mL) was added drop wise 2M iPrMgCl/THF (26.2 ml, 52.4 mmol) at −30° C. over 5 min. Then, the resulting slurry was warmed to −10° C. over 30 min and stirred for 30 min. The homogeneous brown reaction mixture was rapidly transferred via cannula to a solution of ethyl 2-chloro-2-oxoacetate (6.14 ml, 54.9 mmol, degassed for 5 min by bubbling N2 through the solution) in THF (50 mL) maintained at −30° C. The resulting reaction mixture was stirred (1.5 h) while warming to 0° C. Then, taken up in to Et$_2$O (200 mL), washed with 1:1 sat Na$_2$CO$_3$/ 1M NH$_4$Cl (3×50 mL), dried (MgSO$_4$), filtered and concentrated to give brown viscous oil. Flash chromatography using 2.5, 5 and 7.5% EtOAc/Hex afforded ethyl 2-(5-bromo-4-chloro-2,6-dimethylpyridin-3-yl)-2-oxoacetate (14.37 g, 44.8 mmol, 90% yield) as white solid. $^1$H NMR (400 MHz, CDCl$_3$) δ 4.42 (q, J=7.0 Hz, 2H), 2.76 (s, 3H), 2.46 (s, 3H), 1.41 (t, J=7.2 Hz, 3H). LCMS (M+H)=322.1.

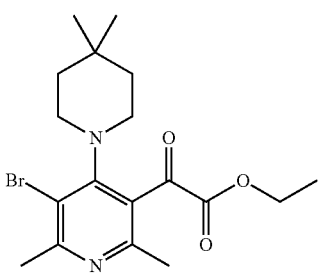 [SMILES: CCOC(=O)C(=O)c1c(C)nc(C)c(Br)c1N1CCC(C)(C)CC1]

Ethyl 2-(5-bromo-4-(4,4-dimethylpiperidin-1-yl)-2,6-dimethylpyridin-3-yl)-2-oxoacetate To a solution of 4,4-dimethylpiperidine (1.245 g, 11.00 mmol) and DIEA (3.49 ml, 20.00 mmol) in anhydrous CH$_3$CN (40 mL) was added ethyl 2-(5-bromo-4-chloro-2,6-dimethylpyridin-3-yl)-2-oxoacetate (3.21 g, 10 mmol) at rt. The resulting mixture was placed in a pre-heated oil bath (80° C.). After 22 h, the reaction mixture was concentrated and the residue was purified by flash chromatography using 1-lit each 2.5, 5, 7.5 and 10% EtOAc/Hex to afford ethyl 2-(5-bromo-4-(4,4-dimethylpiperidin-1-yl)-2,6-dimethylpyridin-3-yl)-2-oxoacetate (2.846 g, 7.16 mmol, 71.6% yield) as yellow solid. $^1$H NMR (500 MHz, CDCl$_3$) δ 4.37 (q, J=7.1 Hz, 2H), 3.67-2.75 (br.s., 4H), 2.71 (s, 3H), 2.44 (s, 3H), 1.42 (t, J=7.1 Hz, 3H), 1.38 (t, J=5.6 Hz, 4H), 1.00 (s, 6H). LCMS (M+H)=399.4.

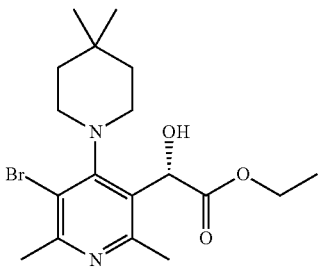 [SMILES: CCOC(=O)[C@@H](O)c1c(C)nc(C)c(Br)c1N1CCC(C)(C)CC1]

(S)-Ethyl 2-(5-bromo-4-(4,4-dimethylpiperidin-1-yl)-2,6-dimethylpyridin-3-yl)-2-hydroxyacetate To stirred yellow solution of ethyl 2-(5-bromo-4-(4,4-dimethylpiperidin-1-yl)-2,6-dimethylpyridin-3-yl)-2-oxoacetate (2.25 g, 5.66 mmol) and (R)-1-methyl-3,3-diphenylhexahydropyrrolo[1,2-c][1,3,2]oxazaborole (0.314 g, 1.133 mmol) in toluene (30 mL) at −35° C. was added drop wise 50% catecholborane (1.819 ml, 8.49 mmol) over 10 min. The reaction mixture was slowly warmed to −15° C. over 1 h and then left for 2 h at −15° C. Then, diluted with EtOAc (100 mL), washed with sat Na$_2$CO$_3$ (4×25 mL) by vigorously stirring and separating aqueous layers. The organic layer dried (MgSO$_4$), filtered, concentrated and purified by flash chromatography using 10, 20 and 25% EtOAc/Hex to afford desired (S)-ethyl 2-(5-bromo-4-(4,4-dimethylpiperidin-1-yl)-2,6-dimethylpyridin-3-yl)-2-hydroxyacetate (2.2596 g, 5.66 mmol, 100% yield) contaminated with about 10% of (S)-ethyl 2-(5-bromo-4-chloro-2,6-dimethylpyridin-3-yl)-2-hydroxyacetate. Used in the next step without further purification. $^1$H NMR (500 MHz, CDCl$_3$) δ 5.71 (d, J=7.3 Hz, 1H), 5.54 (d, J=7.4 Hz, 1H), 4.29 (dq, J=10.8, 7.1 Hz, 1H), 4.16 (dq, J=10.8, 7.1 Hz, 1H), 3.94-3.83 (m, 2H), 2.71 (d, J=11.9 Hz, 1H), 2.67 (s, 3H), 2.59 (s, 3H), 2.54 (d, J=12.0 Hz, 1H), 1.71 (td, J=12.7, 4.7 Hz, 1H), 1.62 (td, J=13.0, 4.7 Hz, 1H), 1.42 (dd, J=13.1, 2.2 Hz, 1H), 1.37 (dd, J=12.9, 2.4 Hz, 1H), 1.25 (t, J=7.1 Hz, 3H), 1.09 (s, 3H), 1.04 (s, 3H). LCMS (M+H)=401.3.

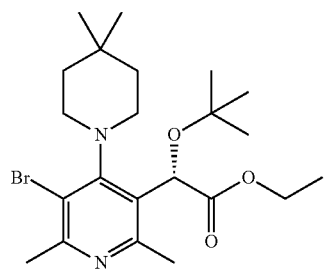 [SMILES: CCOC(=O)[C@@H](OC(C)(C)C)c1c(C)nc(C)c(Br)c1N1CCC(C)(C)CC1]

(S)-Ethyl 2-(5-bromo-4-(4,4-dimethylpiperidin-1-yl)-2,6-dimethylpyridin-3-yl)-2-(tert-butoxy)acetate A stirred ice-cold yellow mixture of (S)-ethyl 2-(5-bromo-4-(4,4-dimethylpiperidin-1-yl)-2,6-dimethylpyridin-3-yl)-2-hydroxyacetate (2.45 g, 6.14 mmol) and 70% HClO$_4$ (1.054 ml, 12.27 mmol) in CH$_2$Cl$_2$ (100 mL) was saturated with isobutylene gas by bubbling through the reaction mixture (10 min). After 2 h, cold bath was removed and the turbid reaction mixture stirred for 22 h at rt. LCMS at this point showed 4:1 product to sm. So, saturated with isobutylene (5 min) at rt and stirred for additional 24 h. Then, neutralized with sat. Na$_2$CO$_3$ (30 mL), organic layer separated and aqueous layer extracted with CH$_2$Cl$_2$ (25 mL). The combined organic layers dried (MgSO$_4$), filtered, concentrated and purified by flash chromatography using 5, 10, 15, 20 and 40% EtOAc/hex to afford (S)-ethyl 2-(5-bromo-4-(4,4-dimethylpiperidin-1-yl)-2,6-dimethylpyridin-3-yl)-2-(tert-butoxy)acetate (2.3074 g, 5.07 mmol, 83% yield) as yellow oil: $^1$H NMR (500 MHz, CDCl$_3$) δ 6.19 (br. s., 1H), 4.17-4.24 (m, 1H), 4.08-4.14 (m, 1H), 4.04 (dt, J=2.5, 12.1 Hz, 1H), 3.51 (dt, J=2.5, 12.1 Hz, 1H), 2.85-2.91 (m, 1H), 2.64 (s, 3H), 2.57-2.62 (m, 1H), 2.55 (s, 3H), 1.55-1.66 (m, 2H), 1.41-1.46 (m, 1H), 1.32-1.37 (m, 1H), 1.21 (s, 9H), 1.20 (t, J=7.2 Hz, 2H), 1.08 (s, 3H), 1.03 (s, 3H). LCMS (M+H)=457.4. And (S)-ethyl 2-(5-bromo-4-(4,4-dimethylpiperidin-1-yl)-2,6-dimethylpyridin-3-yl)-2-hydroxyacetate (0.3 g, 0.751 mmol, 12.24% yield) as pale yellow paste: LCMS (M+H)=401.3.

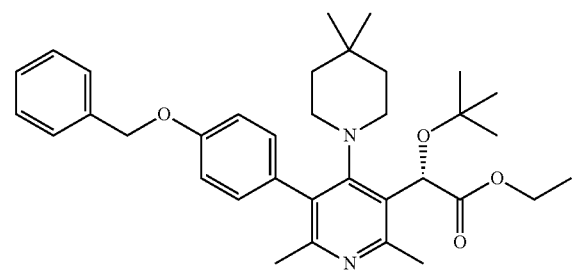 [SMILES: CCOC(=O)[C@@H](OC(C)(C)C)c1c(C)nc(C)c(-c2ccc(OCc3ccccc3)cc2)c1N1CCC(C)(C)CC1]

(S)-Ethyl 2-(5-(4-(benzyloxy)phenyl)-4-(4,4-dimethylpiperidin-1-yl)-2,6-dimethylpyridin-3-yl)-2-(tert-butoxy)acetate A mixture of (S)-ethyl 2-(5-bromo-4-(4,4-dimethylpiperidin-1-yl)-2,6-dimethylpyridin-3-yl)-2-(tert-butoxy)acetate (0.514 g, 1.129 mmol), (4-(benzyloxy)phenyl)boronic acid (0.515 g, 2.257 mmol) and 2M Na$_2$CO$_3$ (1.693 ml, 3.39 mmol) in DMF (10 mL) was degassed for 10 min. Then, Pd(Ph$_3$P)$_4$ (0.065 g, 0.056 mmol) was added, degassed for 5 min and placed in a pre-heated oil bath at 110° C. After 2 h, cooled, diluted with ether (50 mL), washed with water (4×10 mL), brine (10 mL), dried (MgSO$_4$), filtered, concentrated and purified by flash chromatography using 10, 20 and 30% EtOAc/Hex to afford (S)-ethyl 2-(5-(4-(benzyloxy)phenyl)-4-(4,4-dimethylpiperidin-1-yl)-2,6-dimethylpyridin-3-yl)-2-(tert-butoxy)acetate (0.4345 g, 0.778 mmol, 68.9% yield) as white solid. $^1$H NMR (500 MHz, CDCl$_3$) δ 7.48-7.51 (m, 2H), 7.40-7.45 (m, 2H), 7.34-7.38 (m, 1H), 7.16-7.20 (m, 1H), 7.04-7.10 (m, 3H), 6.09 (s, 1H), 5.13-5.20 (m, 2H), 4.26 (qd, J=7.1, 10.7 Hz, 1H), 4.17 (qd, J=7.1, 10.7 Hz, 1H), 3.18 (d, J=11.8 Hz, 1H), 2.87 (t, J=11.8 Hz, 1H), 2.27 (d, J=11.8 Hz, 1H), 2.21 (s, 3H), 2.05 (t, J=11.7 Hz, 1H), 1.56 (dt, J=4.6, 12.9 Hz, 2H), 1.32-1.41 (m, 1H), 1.26 (t, J=7.1 Hz, 3H), 1.21 (s, 9H), 1.18 (br. s., 1H), 1.05-1.11 (m, 1H), 0.91 (s, 3H), 0.64 (s, 3H). LCMS (M+H) 559.5.

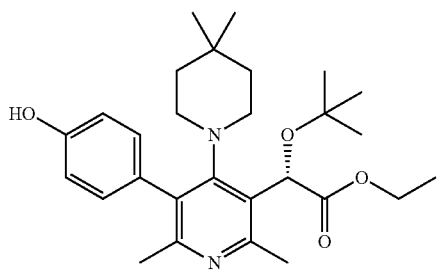 [SMILES: CCOC(=O)[C@@H](OC(C)(C)C)c1c(C)nc(C)c(-c2ccc(O)cc2)c1N1CCC(C)(C)CC1]

(S)-Ethyl 2-(tert-butoxy)-2-(4-(4,4-dimethylpiperidin-1-yl)-5-(4-hydroxyphenyl)-2,6-dimethylpyridin-3-yl)acetate A mixture of (S)-ethyl 2-(5-(4-(benzyloxy)phenyl)-4-(4,4-dimethylpiperidin-1-yl)-2,6-dimethylpyridin-3-yl)-2-(tert-butoxy)acetate (0.434 g, 0.777 mmol) and 10% Pd/C (0.083 g, 0.078 mmol) in EtOAc (25 mL) was evacuated and released to H$_2$ three times and left under balloon H$_2$ atmosphere for h. Then, filtered through a plug of celite and concentrated to afford (S)-ethyl 2-(tert-butoxy)-2-(4-(4,4-dimethylpiperidin-1-yl)-5-(4-hydroxyphenyl)-2,6-dimethylpyridin-3-yl)acetate (0.36 g, 0.768 mmol, 99% yield) as white solid which was used in subsequent reactions without purification. $^1$H NMR (500 MHz, CDCl$_3$) δ 7.11 (dd, J=2.0, 8.6 Hz, 1H), 6.99-7.03 (m, 1H), 6.94 (tdd, J=2.2, 4.4, 6.4 Hz, 2H), 6.09 (s, 1H), 4.23-4.30 (m, 1H), 4.19 (qd, 10.8 Hz, 1H), 3.18 (d, J=11.4 Hz, 1H), 2.88 (t, J=12.1 Hz, 1H), 2.62 (s, 3H), 2.28 (d, J=10.9 Hz, 1H), 2.22 (s, 3H), 2.10 (t, J=11.7 Hz, 1H), 1.51-1.60 (m, 1H), 1.33-1.42 (m, 1H), 1.27 (t, J=7.1 Hz, 3H), 1.21 (s, 9H), 1.18-1.20 (m, 1H), 1.09 (d, J=9.9 Hz, 1H), 0.91 (br. s., 3H), 0.66 (br. s., 3H). LCMS (M+H)=469.3.

Alternative Procedure:

A mixture of (S)-ethyl 2-(5-bromo-4-(4,4-dimethylpiperidin-1-yl)-2,6-dimethylpyridin-3-yl)-2-(tert-butoxy)acetate (2.5 g, 5.49 mmol), (4-((tert-butyldimethylsilyl)oxy)phenyl)boronic acid (2.77 g, 10.98 mmol) and 2M Na$_2$CO$_3$ (6.86 mL, 13.72 mmol) in 1,4-dioxane (50 mL) was degassed for 10 min. Then, Pd(Ph$_3$P)$_4$ (0.317 g, 0.274 mmol) was added, degassed for 5 min and placed in a pre-heated oil bath at 90° C. After 16 h, the reaction mixture was diluted with ethyl acetate (100 mL), washed with water (4×25 mL) and brine (25 mL), dried (Na$_2$SO$_4$), filtered, concentrated and the brown residue was treated with 1M TBAF (10.98 mL, 10.98 mmol) in THF (50 mL) at room temp for 1 h. Mixture was then concentrated and purified by Biotage (5-50% EtOAc/hexane) to afford (S)-ethyl 2-(tert-butoxy)-2-(4-(4,4-dimethylpiperidin-1-yl)-5-(4-hydroxyphenyl)-2,6-dimethylpyridin-3-yl)acetate (1.6 g, 3.41 mmol, 62.2% yield) as off-white solid. LCMS (M+H)=469.3.

Example 1

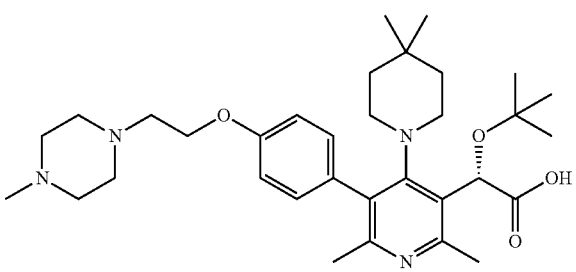

(S)-2-(tert-Butoxy)-2-(4-(4,4-dimethylpiperidin-1-yl)-2,6-dimethyl-5-(4-(2-(4-methylpiperazin-1-yl)ethoxy)phenyl)pyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-methylpiperazin-1-yl)ethanol (30.8 mg, 0.213 mmol) and Ph$_3$P-resin (33.6 mg, 0.128 mmol) in THF (5 mL) was added DEAD (0.020 mL, 0.128 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-(4-methylpiperazin-1-yl)ethoxy)phenyl)pyridin-3-yl)acetic acid (2.1 mg, 3.71 μmol, 8.68% yield). $^1$H NMR (500 MHz, DMSO-d$_6$) δ 7.21 (d, J=8.4 Hz, 1H), 7.05-7.00 (m, 3H), 5.80 (s, 1H), 4.22-4.04 (m, 2H), 3.36 (br. s., 1H), 2.84-2.76 (m, 1H), 2.70 (t, J=5.7 Hz, 2H), 2.43 (s, 3H), 2.33 (br. s., 3H), 2.16 (s, 3H), 2.06 (s, 3H), 1.49 (br. s., 1H), 1.30 (br. s., 1H), 1.17 (d, J=11.4 Hz, 1H), 1.12 (s, 9H), 1.02 (d, J=12.5 Hz, 1H), 0.85 (s, 3H), 0.61 (s, 3H). 8H of piperidine were not resolved. LCMS (M+H)=567.5

Example 2

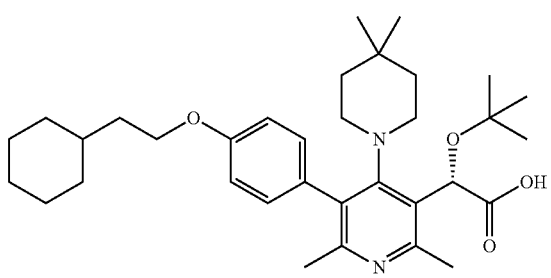 [SMILES: Cc1nc(C)c([C@H](OC(C)(C)C)C(=O)O)c(N2CCC(C)(C)CC2)c1-c1ccc(OCCC2CCCCC2)cc1]

(S)-2-(tert-Butoxy)-2-(5-(4-(2-cyclohexylethoxy)phenyl)-4-(4,4-dimethylpiperidin-1-yl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-cyclohexylethanol (27.4 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(5-(4-(2-cyclohexylethoxy)phenyl)-4-(4,4-dimethylpiperidin-1-yl)-2,6-dimethylpyridin-3-yl)acetic acid (6.3 mg, 0.011 mmol, 26.8% yield). $^1$H NMR (500 MHz, DMSO-d$_6$) δ 7.20 (d, J=7.3 Hz, 1H), 7.07-6.98 (m, 3H), 5.84 (br. s., 1H), 4.15-3.97 (m, 2H), 3.35 (br. s., 1H), 3.26 (br. s., 1H), 2.80 (t, J=12.1 Hz, 1H), 2.43 (s, 3H), 2.18 (d, J=10.3 Hz, 1H), 2.06 (s, 3H), 1.98-1.89 (m, 1H), 1.75 (d, J=12.1 Hz, 2H), 1.71-1.58 (m, 5H), 1.49 (br. s., 2H), 1.35-1.16 (m, 4H), 1.13 (s, 9H), 1.05-0.91 (m, 3H), 0.85 (s, 3H), 0.61 (s, 3H). LCMS (M+H)=551.25.

Example 3

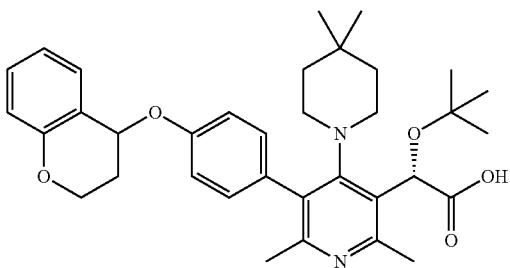 [SMILES: Cc1nc(C)c([C@H](OC(C)(C)C)C(=O)O)c(N2CCC(C)(C)CC2)c1-c1ccc(OC2CCOc3ccccc32)cc1]

(2S)-2-(tert-Butoxy)-2-(5-(4-(chroman-4-yloxy)phenyl)-4-(4,4-dimethylpiperidin-1-yl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), chroman-4-ol (32.0 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (2S)-2-(tert-butoxy)-2-(5-(4-(chroman-4-yloxy)phenyl)-4-(4,4-dimethylpiperidin-1-yl)-2,6-dimethylpyridin-3-yl)acetic acid (7.1 mg, 0.012 mmol, 29.0% yield). $^1$H NMR (500 MHz, DMSO-d$_6$) δ 7.34-7.22 (m, 4H), 7.18 (dd, J=8.4, 2.6 Hz, 1H), 7.10 (d, J=8.8 Hz, 1H), 6.95-6.83 (m, 2H), 5.83 (br. s., 1H), 5.59 (d, J=10.6 Hz, 1H), 4.33-4.26 (m, 1H), 4.26-4.14 (m, 1H), 3.55-3.25 (m., 2H), 2.82 (t, J=12.1 Hz, 1H), 2.45 (s, 3H), 2.27-2.13 (m, 3H), 1.95 (d, J=13.6 Hz, 1H), 1.50 (br. s., 1H), 1.31 (br. s., 1H), 1.19 (d, J=12.8 Hz, 1H), 1.13 (s, 9H), 1.04 (d, J=10.6 Hz, 1H), 0.86 (s., 3H), 0.63 (d, J=13.2 Hz, 3H). LCMS (M+H)=573.20.

Example 4

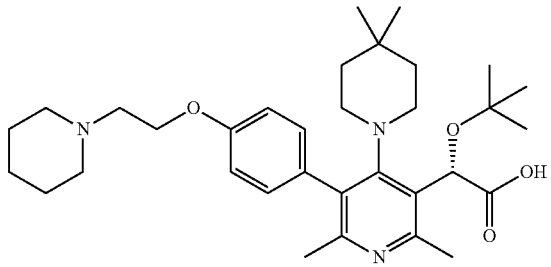 [SMILES: Cc1nc(C)c([C@H](OC(C)(C)C)C(=O)O)c(N2CCC(C)(C)CC2)c1-c1ccc(OCCN2CCCCC2)cc1]

(S)-2-(tert-Butoxy)-2-(4-(4,4-dimethylpiperidin-1-yl)-2,6-dimethyl-5-(4-(2-(piperidin-1-yl)ethoxy)phenyl)pyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(piperidin-1-yl)ethanol (27.6 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-(piperidin-1-yl)ethoxy)phenyl)pyridin-3-yl)acetic acid (13.8 mg, 0.025 mmol, 58.6% yield). $^1$H NMR (500 MHz, DMSO-d$_6$) δ 7.20 (d, J=8.8 Hz, 1H), 7.08-6.91 (m, 3H), 5.83 (s, 1H), 4.19-4.08 (m, 2H), 3.30 (br. s., 2H), 2.80 (t, J=11.4 Hz, 1H), 2.68 (t, J=5.9 Hz, 2H), 2.47-2.37 (m, 6H), 2.17 (d, J=11.4 Hz, 1H), 2.08-2.04 (m, 3H), 1.98-1.92 (m, 1H), 1.56-1.44 (m, 5H), 1.38 (br. s., 2H), 1.28 (d, J=8.8 Hz, 1H), 1.18 (d, J=12.1 Hz, 1H), 1.12 (s, 9H), 1.02 (d, J=13.9 Hz, 1H), 0.85 (s, 3H), 0.61 (s, 3H). LCMS (M+H)=552.5.

Example 5

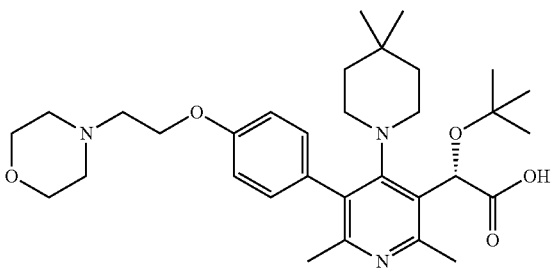 [SMILES: Cc1nc(C)c([C@H](OC(C)(C)C)C(=O)O)c(N2CCC(C)(C)CC2)c1-c1ccc(OCCN2CCOCC2)cc1]

(S)-2-(tert-Butoxy)-2-(4-(4,4-dimethylpiperidin-1-yl)-2,6-dimethyl-5-(4-(2-morpholinoethoxy)phenyl)pyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-morpholinoethanol (28.0 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-morpholinoethoxy)phenyl)pyridin-3-yl)acetic acid (8.8 mg, 0.016 mmol, 37.2% yield). $^1$H NMR (500 MHz, DMSO-$d_6$) δ 7.21 (d, J=9.2 Hz, 1H), 7.10-6.95 (m, 3H), 5.83 (s, 1H), 4.24-4.07 (m, 2H), 3.28 (d, J=10.6 Hz, 2H), 2.80 (t, J=11.7 Hz, 1H), 2.71 (t, J=5.7 Hz, 2H), 2.48 (br. s., 3H), 2.43 (s, 3H), 2.18 (d, J=9.9 Hz, 1H), 2.09-2.03 (m, 3H), 1.99-1.93 (m, 1H), 1.49 (br. s., 1H), 1.29 (br. s., 1H), 1.18 (d, J=11.4 Hz, 1H), 1.13 (s, 9H), 1.02 (d, J=12.5 Hz, 1H), 0.85 (s, 3H), 0.61 (s, 3H). 4H of piperidine not resolved. LCMS (M+H)=554.5.

Example 6

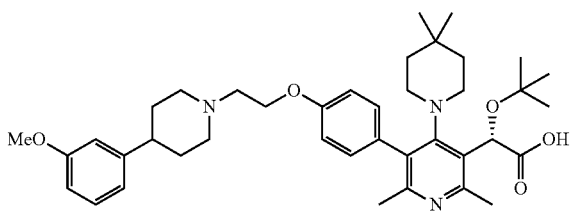 [SMILES: COc1cccc(C2CCN(CCOc3ccc(-c4c(C)nc(C)c([C@H](OC(C)(C)C)C(=O)O)c4N4CCC(C)(C)CC4)cc3)CC2)c1]

(S)-2-(tert-Butoxy)-2-(4-(4,4-dimethylpiperidin-1-yl)-5-(4-(2-(4-(3-methoxyphenyl)piperidin-1-yl)ethoxy)phenyl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-(3-methoxyphenyl)piperidin-1-yl)ethanol (50.2 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-5-(4-(2-(4-(3-methoxyphenyl)piperidin-1-yl)ethoxy)phenyl)-2,6-dimethylpyridin-3-yl)acetic acid (8.8 mg, 0.013 mmol, 31.3% yield). $^1$H NMR (500 MHz, DMSO-$d_6$) δ 7.26-7.17 (m, 2H), 7.09-6.96 (m, 3H), 6.86-6.78 (m, 2H), 6.77-6.71 (m, 1H), 5.83 (s, 1H), 4.23-4.11 (m, 2H), 3.31 (br. s., 2H), 3.07 (d, J=10.6 Hz, 2H), 2.85-2.80 (m, 1H), 2.76 (t, J=5.7 Hz, 2H), 2.47 (br. s., 1H), 2.44 (s, 3H), 2.23-2.12 (m, 4H), 2.07 (s, 3H), 2.00-1.93 (m, 1H), 1.78-1.71 (m, 3H), 1.71-1.63 (m, 2H), 1.50 (br. s., 1H), 1.30 (br. s., 1H), 1.18 (d, J=13.2 Hz, 1H), 1.13 (s, 9H), 1.03 (d, J=12.1 Hz, 1H), 0.85 (s, 3H), 0.62 (s, 3H). LCMS (M+H)=658.35.

Example 7

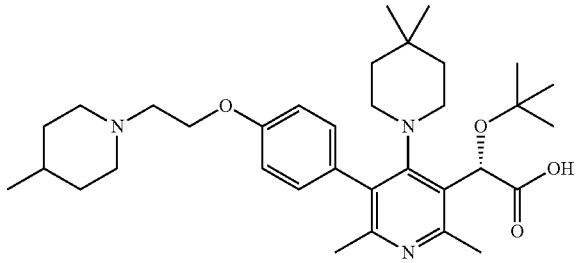 [SMILES: Cc1nc(C)c([C@H](OC(C)(C)C)C(=O)O)c(N2CCC(C)(C)CC2)c1-c1ccc(OCCN2CCC(C)CC2)cc1]

(S)-2-(tert-Butoxy)-2-(4-(4,4-dimethylpiperidin-1-yl)-2,6-dimethyl-5-(4-(2-(4-methylpiperidin-1-yl)ethoxy)phenyl)pyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-methylpiperidin-1-yl)ethanol (30.6 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-(4-methylpiperidin-1-yl)ethoxy)phenyl)pyridin-3-yl)acetic acid (5.7 mg, 10.07 μmol, 23.61% yield). $^1$H NMR (500 MHz, DMSO-$d_6$) δ 7.20 (d, J=8.4 Hz, 1H), 7.10-6.91 (m, 3H), 5.76 (s, 1H), 4.23-4.03 (m, 1H), 3.41 (d, J=9.5 Hz, 1H), 2.83-2.77 (m, 1H), 2.70 (t, J=5.7 Hz, 2H), 2.43 (s, 3H), 2.17 (d, J=11.0 Hz, 1H), 2.06 (s, 3H), 2.04-1.99 (m, 2H), 1.96-1.91 (m, 1H), 1.57 (d, J=12.1 Hz, 2H), 1.50 (br. s., 1H), 1.39-1.25 (m, 2H), 1.20-1.13 (m, 2H), 1.12 (s, 9H), 1.01 (d, J=11.4 Hz, 1H), 0.89 (d, J=6.6 Hz, 3H), 0.85 (s, 3H), 0.61 (s., 3H). 4H of piperidine were not resolved. LCMS (M+H)=566.6.

Example 8 and 9

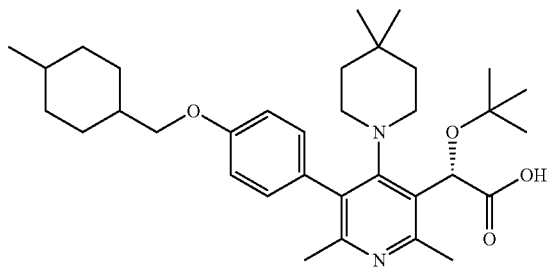 [SMILES: Cc1nc(C)c([C@H](OC(C)(C)C)C(=O)O)c(N2CCC(C)(C)CC2)c1-c1ccc(OCC2CCC(C)CC2)cc1]

(S)-2-(tert-Butoxy)-2-(4-(4,4-dimethylpiperidin-1-yl)-2,6-dimethyl-5-(4-((4-methylcyclohexyl)methoxy)phenyl)pyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), (4-methylcyclohexyl)methanol (27.4 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford two isomers of (S)-2-(tert-butoxy)-2-(4-(4,4-dimethylpiperidin-1-yl)-2,6-dimethyl-5-(4-((4-methylcyclohexyl)methoxy)phenyl)pyridin-3-yl)acetic acid.

Example 8

(2.2 mg, 3.99 µmol, 9.36% yield). $^1$H NMR (500 MHz, DMSO-$d_6$) δ 7.19 (d, J=7.7 Hz, 1H), 7.07-6.98 (m, 3H), 5.78 (s, 1H), 3.99-3.89 (m, 3H), 3.49-3.35 (m, 2H), 2.78 (t, J=12.5 Hz, 1H), 2.43 (s, 3H), 2.17 (d, J=11.7 Hz, 1H), 2.06 (s, 3H), 1.98-1.88 (m, 3H), 1.65 (d, J=6.6 Hz, 1H), 1.59-1.43 (m, 5H), 1.34-1.23 (m, 2H), 1.17 (d, J=13.2 Hz, 1H), 1.12 (s, 9H), 1.01 (d, J=11.7 Hz, 1H), 0.92 (d, J=7.0 Hz, 3H), 0.85 (br. s., 3H), 0.61 (br. s., 3H). LCMS (M+H)=551.5.

Example 9

(1.3 mg, 2.360 µmol, 5.53% yield). $^1$H NMR (500 MHz, DMSO-$d_6$) δ 7.20 (d, J=7.7 Hz, 1H), 7.07-6.98 (m, 3H), 5.80 (br. s., 1H), 3.91 (s, 1H), 3.88-3.78 (m, 2H), 3.34 (br. s., 1H), 2.79 (t, J=11.6 Hz, 1H), 2.43 (s, 3H), 2.17 (d, J=12.5 Hz, 1H), 2.06 (s, 3H), 1.97-1.91 (m, 1H), 1.84 (d, J=12.8 Hz, 2H), 1.71 (d, J=11.7 Hz, 3H), 1.51 (d, J=9.9 Hz, 1H), 1.31 (d, J=15.4 Hz, 2H), 1.19 (br. s., 1H), 1.12 (s, 9H), 1.09-1.00 (m, 2H), 0.99-0.91 (m, 2H), 0.89 (d, J=6.6 Hz, 3H), 0.85 (br. s., 3H), 0.61 (s, 3H). LCMS (M+H)=551.5.

Example 10

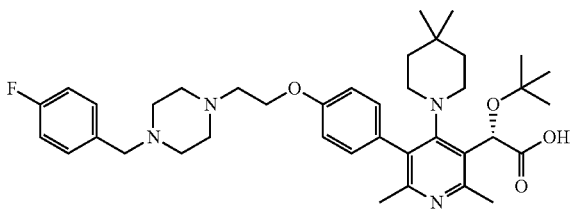 [SMILES: Cc1nc(C)c([C@H](OC(C)(C)C)C(=O)O)c(N2CCC(C)(C)CC2)c1-c1ccc(OCCN2CCN(Cc3ccc(F)cc3)CC2)cc1]

(S)-2-(tert-Butoxy)-2-(4-(4,4-dimethylpiperidin-1-yl)-5-(4-(2-(4-(4-fluorobenzyl)piperazin-1-yl)ethoxy)phenyl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-(4-fluorobenzyl)piperazin-1-yl)ethanol (50.9 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-5-(4-(2-(4-(4-fluorobenzyl)piperazin-1-yl)ethoxy)phenyl)-2,6-dimethylpyridin-3-yl)acetic acid (9.7 mg, 0.015 mmol, 34.4% yield). $^1$H NMR (500 MHz, DMSO-$d_6$) δ 7.36-7.29 (m, 3H), 7.20 (d, J=8.8 Hz, 1H), 7.14 (t, J=8.8 Hz, 2H), 7.07-6.98 (m, 3H), 5.82 (s, 1H), 4.19-4.06 (m, 2H), 3.30 (d, J=13.6 Hz, 3H), 2.85-2.76 (m, 1H), 2.71 (t, J=5.7 Hz, 2H), 2.37 (br. s., 3H), 2.17 (d, J=10.3 Hz, 1H), 1.95 (br. s., 1H), 1.49 (br. s., 1H), 1.30 (br. s., 1H), 1.17 (d, J=11.4 Hz, 1H), 1.12 (s, 9H), 1.01 (d, J=13.9 Hz, 1H), 0.85 (s, 3H), 0.60 (s, 3H). 10H of piperidine and piperazine were not resolved. LCMS (M+H)=661.3.

Example 11

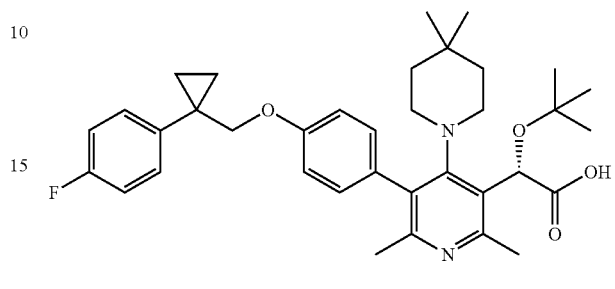

(S)-2-(tert-Butoxy)-2-(4-(4,4-dimethylpiperidin-1-yl)-5-(4-(0-(4-fluorophenyl)cyclopropyl)methoxy)phenyl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), (1-(4-fluorophenyl)cyclopropyl)methanol (35.5 mg, 0.213 mmol) and Ph$_3$P-resin (56.0 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-5-(4-((1-(4-fluorophenyl)cyclopropyl)methoxy)phenyl)-2,6-dimethylpyridin-3-yl)acetic acid (10.5 mg, 0.018 mmol, 41.8% yield). $^1$H NMR (500 MHz, DMSO-$d_6$) δ 7.41 (dd, J=8.4, 5.5 Hz, 2H), 7.18 (d, J=8.1 Hz, 1H), 7.12 (t, J=8.8 Hz, 2H), 7.03-6.90 (m, 3H), 5.75 (br. s., 1H), 4.18-4.07 (m, 2H), 2.81-2.74 (m, 1H), 2.42 (s, 3H), 2.14 (br. s., 1H), 2.03 (s, 3H), 1.90 (br. s, 2H), 1.49 (br. s., 1H), 1.28 (br. s., 1H), 1.16 (d, J=13.6 Hz, 1H), 1.11 (s, 9H), 1.06-0.97 (m, 3H), 0.93 (s, 2H), 0.84 (s, 3H), 0.60 (s, 3H). LCMS (M+H)=589.5.

Example 12

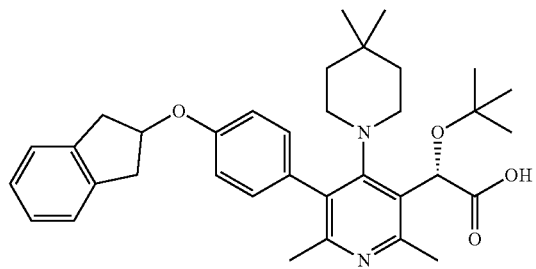 [SMILES: Cc1nc(C)c([C@H](OC(C)(C)C)C(=O)O)c(N2CCC(C)(C)CC2)c1-c1ccc(OC2Cc3ccccc3C2)cc1]

(S)-2-(tert-Butoxy)-2-(5-(4-((2,3-dihydro-1H-inden-2-yl)oxy)phenyl)-4-(4,4-dimethylpiperidin-1-yl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2,3-dihydro-1H-inden-2-ol (28.6 mg, 0.213 mmol) and Ph₃P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(5-(4-((2,3-dihydro-1H-inden-2-yl)oxy)phenyl)-4-(4,4-dimethylpiperidin-1-yl)-2,6-dimethylpyridin-3-yl)acetic acid (5.9 mg, 10.60 μmol, 24.83% yield). ¹H NMR (500 MHz, DMSO-d₆) δ 7.33-7.16 (m, 5H), 7.07 (s, 2H), 7.02 (d, J=8.4 Hz, 1H), 5.85 (br. s., 1H), 5.32 (br. s., 1H), 3.44-3.34 (m, 2H), 3.29 (br. s., 2H), 3.12-3.00 (m, 1H), 2.82 (br. s., 1H), 2.44 (br. s., 3H), 2.18 (d, J=9.5 Hz, 1H), 2.09 (s, 3H), 1.99-1.87 (m, 1H), 1.50 (br. s., 1H), 1.31 (br. s., 1H), 1.20 (br. s., 1H), 1.13 (s, 9H), 1.04 (d, J=11.7 Hz, 1H), 0.87 (br. s., 3H), 0.65 (s, 3H). LCMS (M+H)=557.5.

Example 13

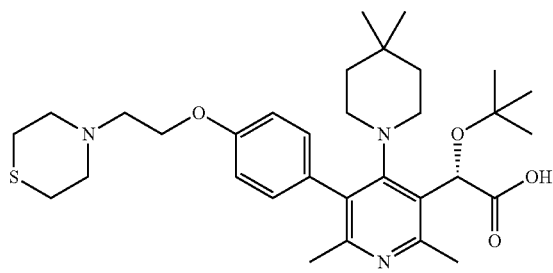 [SMILES: Cc1nc(C)c([C@H](OC(C)(C)C)C(=O)O)c(N2CCC(C)(C)CC2)c1-c1ccc(OCCN2CCSCC2)cc1]

(S)-2-(tert-Butoxy)-2-(4-(4,4-dimethylpiperidin-1-yl)-2,6-dimethyl-5-(4-(2-thiomorpholinoethoxy)phenyl)pyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (25 mg, 0.053 mmol), 2-thiomorpholinoethanol (23.56 mg, 0.160 mmol) and Ph₃P-resin (69.7 mg, 0.267 mmol) in THF (2 mL) was added DEAD (0.025 mL, 0.160 mmol) at rt. After 18 h, mixture was filtered to remove polymer, concentrated and treated with 1N NaOH (1.067 mL, 1.067 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-thiomorpholinoethoxy)phenyl)pyridin-3-yl)acetic acid (21.6 mg, 0.038 mmol, 71.1% yield). ¹H NMR (500 MHz, DMSO-d₆) δ 7.21 (d, J=8.4 Hz, 1H), 7.09-6.99 (m, 3H), 5.85 (br. s., 1H), 4.19-4.07 (m, 2H), 3.24 (br. s., 1H), 2.84-2.71 (m, 8H), 2.64-2.58 (m, 3H), 2.43 (s, 3H), 2.18 (d, J=9.2 Hz, 1H), 2.06 (s, 3H), 1.99-1.93 (m, 1H), 1.49 (br. s., 1H), 1.29 (br. s., 1H), 1.18 (d, J=12.1 Hz, 1H), 1.13 (s, 9H), 1.02 (d, J=11.0 Hz, 1H), 0.85 (br. s., 3H), 0.61 (br. s., 3H). LCMS (M+H)=570.6.

Example 14

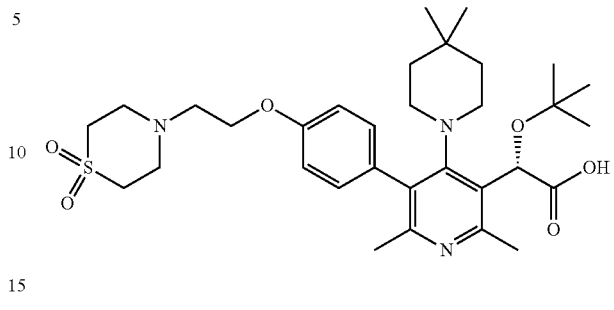

(S)-2-(tert-Butoxy)-2-(4-(4,4-dimethylpiperidin-1-yl)-5-(4-(2-(1,1-dioxidothiomorpholino)ethoxy)phenyl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (25 mg, 0.053 mmol), 4-(2-hydroxyethyl)thiomorpholine 1,1-dioxide (28.7 mg, 0.160 mmol) and Ph₃P-resin (69.7 mg, 0.267 mmol) in THF (2 mL) was added DEAD (0.025 mL, 0.160 mmol) at rt. After 18 h, mixture was filtered to remove polymer, concentrated and treated with 1N NaOH (1.067 mL, 1.067 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-5-(4-(2-(1,1-dioxidothiomorpholino)ethoxy)phenyl)-2,6-dimethylpyridin-3-yl)acetic acid (13.9 mg, 0.023 mmol, 43.3% yield). ¹H NMR (500 MHz, DMSO-d₆) δ 7.22 (d, J=7.7 Hz, 1H), 7.11-6.94 (m, 3H), 5.85 (br. s., 1H), 4.22-4.06 (m, 2H), 3.26 (d, J=8.1 Hz, 1H), 3.10-3.06 (m, 8H), 2.95 (t, J=5.3 Hz, 2H), 2.80 (t, J=11.9 Hz, 1H), 2.43 (s, 3H), 2.17 (br. s., 1H), 2.06 (s, 3H), 1.98-1.93 (m, 1H), 1.49 (br. s., 1H), 1.30 (br. s., 1H), 1.18 (d, J=11.7 Hz, 1H), 1.13 (s, 9H), 1.03 (d, J=12.8 Hz, 1H), 0.85 (br. s., 3H), 0.61 (br. s., 3H). LCMS (M+H)=602.6.

Example 15

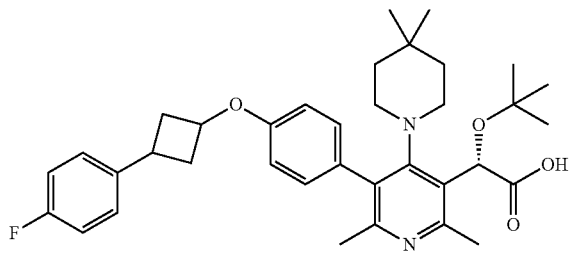 [SMILES: Cc1nc(C)c([C@H](OC(C)(C)C)C(=O)O)c(N2CCC(C)(C)CC2)c1-c1ccc(OC2CC(c3ccc(F)cc3)C2)cc1]

(S)-2-(tert-Butoxy)-2-(4-(4,4-dimethylpiperidin-1-yl)-5-(4-(3-(4-fluorophenyl)cyclobutoxy)phenyl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (50 mg, 0.107 mmol), 3-(4-fluorophenyl)cyclobutanol (89 mg, 0.533 mmol) and Ph₃P (140 mg, 0.533 mmol) in THF (3 mL) was added DIAD (0.104 mL, 0.533 mmol) at rt and the mixture was heated at 70° C.

for 16 h. The reaction mixture was then cooled, concentrated and purified by prep-HPLC to afford desired ester, LCMS (M+H)=617.8. Ester was the treated with 1N NaOH (0.533 mL, 0.533 mmol) in MeOH (2 mL) at 75° C. for 16 h. Mixture was then cooled and purified by prep-HPLC to afford (S)-2-(tert-butoxy)-2-(4-(4,4-dimethylpiperidin-1-yl)-5-(4-(3-(4-fluorophenyl)cyclobutoxy)phenyl)-2,6-dimethylpyridin-3-yl)acetic acid (20 mg, 0.034 mmol, 31.8% yield). $^1$H NMR (500 MHz, DMSO-$d_6$) δ 7.43-7.37 (m, 2H), 7.22 (d, J=7.3 Hz, 1H), 7.16 (t, J=9.0 Hz, 2H), 7.06 (d, J=7.7 Hz, 1H), 6.99-6.91 (m, 2H), 5.83 (s, 1H), 5.04-4.93 (m, 1H), 3.77-3.65 (m, 1H), 3.28 (d, J=10.6 Hz, 1H), 2.80 (t, J=11.7 Hz, 1H), 2.64-2.54 (m, 3H), 2.44 (s, 2H), 2.16 (br. s., 1H), 2.08 (s, 3H), 1.91 (s, 3H), 1.48 (d, J=9.9 Hz, 1H), 1.29 (br. s., 1H), 1.17 (d, J=12.1 Hz, 1H), 1.13 (s, 9H), 1.02 (d, J=12.5 Hz, 1H), 0.85 (br. s., 3H), 0.61 (br. s., 3H). LCMS (M+H)=589.4.

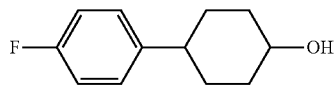 [SMILES: OC1CCC(c2ccc(F)cc2)CC1]

4-(4-Fluorophenyl)cyclohexanol

To a solution of 4-(4-fluorophenyl)cyclohexanone (200 mg, 1.040 mmol) in MeOH (5 mL) was added NaBH$_4$ (59.0 mg, 1.561 mmol) and the mixture was stirred at room temp for 1 h. Water was then added and the mixture was extracted with ethyl acetate, dried (Na$_2$SO$_4$), filtered and concentrated. The residue was then purified by Biotage (5-7-% EtOAc/hexane) to afford 4-(4-fluorophenyl)cyclohexanol (150 mg, 0.772 mmol, 74.2% yield). $^1$H NMR (500 MHz, CDCl$_3$) δ 7.17 (dd, J=8.5, 5.5 Hz, 2H), 7.04-6.92 (m, 2H), 3.78-3.56 (m, 1H), 2.54-2.41 (m, 1H), 2.19-2.09 (m, 2H), 1.97-1.90 (m, 2H), 1.56-1.40 (m, 5H).

Example 16

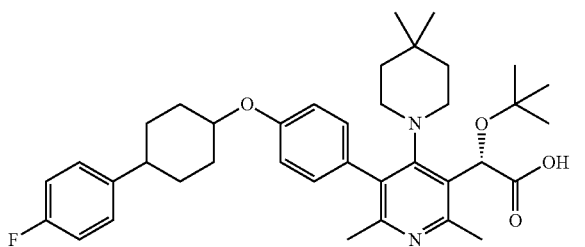 [SMILES: Cc1nc(C)c([C@H](OC(C)(C)C)C(=O)O)c(N2CCC(C)(C)CC2)c1-c1ccc(OC2CCC(c3ccc(F)cc3)CC2)cc1]

(S)-2-(tert-Butoxy)-2-(4-(4,4-dimethylpiperidin-1-yl)-5-(4-((4-(4-fluorophenyl)cyclohexyl)oxy)phenyl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (50 mg, 0.107 mmol), 4-(4-fluorophenyl)cyclohexanol (104 mg, 0.533 mmol) and Ph$_3$P (140 mg, 0.533 mmol) in THF (3 mL) was added DIAD (0.104 mL, 0.533 mmol) at rt and the mixture was heated at 70° C. for 16 h. The reaction mixture was then cooled, concentrated and purified by prep-HPLC to afford desired ester, LCMS (M+H)=645.5. Ester was the treated with 1N NaOH (0.533 mL, 0.533 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-5-(4-((4-(4-fluorophenyl)cyclohexyl)oxy)phenyl)-2,6-dimethylpyridin-3-yl)acetic acid (20.6 mg, 0.033 mmol, 31.3% yield). $^1$H NMR (500 MHz, DMSO-$d_6$) δ 7.33-7.25 (m, 2H), 7.25-7.18 (m, 1H), 7.11 (t, J=8.4 Hz, 4H), 7.04 (d, J=7.7 Hz, 1H), 5.79 (s, 1H), 4.75 (br. s., 1H), 3.34 (d, J=8.8 Hz, 1H), 2.79 (t, J=11.6 Hz, 1H), 2.66 (t, J=11.9 Hz, 1H), 2.44 (s, 3H), 2.16 (d, J=10.3 Hz, 1H), 2.09 (s, 3H), 2.08-2.02 (m, 2H), 1.90-1.73 (m, 3H), 1.73-1.67 (m, 2H), 1.60 (br. s., 2H), 1.47 (br. s., 1H), 1.27 (d, J=7.3 Hz, 1H), 1.16 (br. s., 1H), 1.11 (s, 9H), 0.97 (d, J=11.7 Hz, 1H), 0.82 (br. s., 3H), 0.56 (br. s., 3H). LCMS (M+H)=617.2.

Example 17 and 18

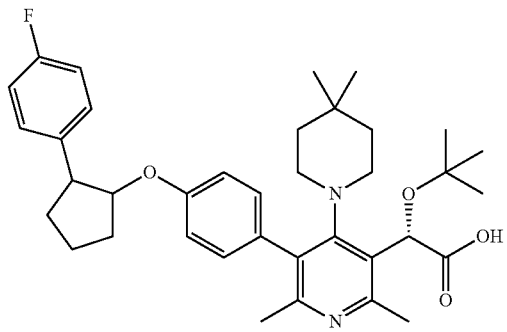

Example 17

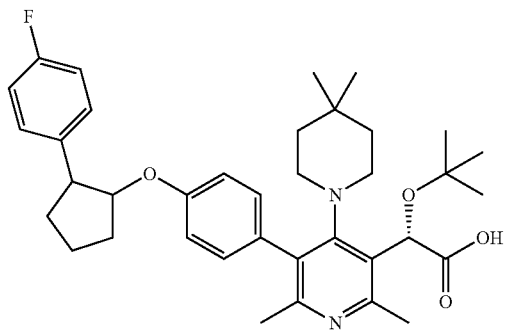

Example 18

(2S)-2-(tert-Butoxy)-2-(4-(4,4-dimethylpiperidin-1-yl)-5-(4-((2-(4-fluorophenyl)cyclopentyl)oxy)phenyl)-2,6-dimethylpyridin-3-yl)acetic Acid To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (50 mg, 0.107 mmol), trans-2-(4-fluorophenyl)cyclopentanol (96 mg, 0.533 mmol, for preparation see Shepherd, T. A. et. al. J. Med. Chem. 2002, 45, 2101-2111) and Ph$_3$P (140 mg, 0.533 mmol) in THF (3 mL) was added DIAD (0.104 mL, 0.533 mmol) at rt and the mixture was heated at 70° C. for 16 h. The reaction mixture was then cooled, concentrated and purified by prep-HPLC to afford desired ester, LCMS (M+H)=631.5. Ester was the treated with 1N NaOH (0.533 mL, 0.533 mmol) in MeOH (2 mL) at 75° C. for 16 h. Mixture was then cooled and purified by prep-HPLC to afford two diasteromers.

Example 17: First Eluting Diatereomer (2S)-2-(tert-Butoxy)-2-(4-(4,4-dimethylpiperidin-1-yl)-5-(4-((2-(4-fluorophenyl)cyclopentyl)oxy)phenyl)-2,6-dimethylpyridin-3-yl)acetic acid (3.4 mg, 5.64 µmol, 5.29% yield): $^1$H NMR (500 MHz, DMSO-d$_6$) δ 7.43-7.33 (m, 2H), 7.15-7.02 (m, 3H), 6.97-6.93 (m, 1H), 6.89-6.81 (m, 2H), 5.84 (s, 1H), 4.94 (br. s., 1H), 3.36 (br. s., 1H), 3.28 (br. s., 1H), 3.20 (d, J=8.8 Hz, 1H), 2.75 (t, J=11.7 Hz, 1H), 2.43 (s, 3H), 2.21-2.05 (m, 3H), 2.02 (s, 3H), 1.95-1.82 (m, 3H), 1.80-1.67 (m, 1H), 1.46 (br. s., 1H), 1.26 (d, J=16.9 Hz, 1H), 1.17 (br. s., 1H), 1.12 (s, 9H), 1.00 (d, J=11.0 Hz, 1H), 0.84 (br. s., 3H), 0.57 (br. s., 3H). LCMS (M+H)=603.1.

Example 18: Second Eluting Diastereomer (2S)-2-(tert-Butoxy)-2-(4-(4,4-dimethylpiperidin-1-yl)-5-(4-((2-(4-fluorophenyl)cyclopentyl)oxy)phenyl)-2,6-dimethylpyridin-3-yl)acetic acid (5.3 mg, 8.79 µmol, 8.24% yield): $^1$H NMR (500 MHz, DMSO-d$_6$) δ 7.40 (t, J=6.8 Hz, 2H), 7.13-7.02 (m, 3H), 6.99-6.86 (m, 2H), 6.81 (d, J=8.1 Hz, 1H), 5.80 (br. s., 1H), 4.95 (br. s., 1H), 3.40 (br. s., 1H), 3.27 (br. s., 2H), 2.82-2.71 (m, 1H), 2.42 (s, 3H), 2.10 (dd, J=16.5, 7.3 Hz, 4H), 2.03 (s, 3H), 1.95-1.82 (m, 2H), 1.78-1.68 (m, 1H), 1.46 (br. s., 1H), 1.25 (d, J=12.5 Hz, 1H), 1.16 (d, J=11.7 Hz, 1H), 1.11 (s, 9H), 0.99 (d, J=12.5 Hz, 1H), 0.84 (br. s., 3H), 0.57 (br. s., 3H). LCMS (M+H)=603.2.

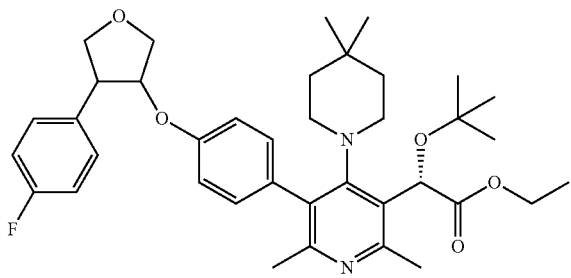

(2S)-ethyl 2-(tert-butoxy)-2-(4-(4,4-dimethylpiperidin-1-yl)-5-(4-((4-(4-fluorophenyl)tetrahydrofuran-3-yl)oxy)phenyl)-2,6-dimethylpyridin-3-yl)acetate To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (200 mg, 0.427 mmol), 4-(4-fluorophenyl)tetrahydrofuran-3-ol (389 mg, 2.134 mmol, for preparation see J. Med. Chem. 2011, 54, 8480-8500) and Ph$_3$P (560 mg, 2.134 mmol) in THF (3 mL) was added DIAD (0.415 mL, 2.134 mmol) at rt and the mixture was heated at 70° C. for 16 h. The reaction mixture was then cooled, concentrated and purified by prep-HPLC to afford (2S)-ethyl 2-(tert-butoxy)-2-(4-(4,4-dimethylpiperidin-1-yl)-5-(4-((4-(4-fluorophenyl)tetrahydrofuran-3-yl)oxy)phenyl)-2,6-dimethylpyridin-3-yl)acetate (130 mg, 0.205 mmol, 48.1% yield) as mixture of diastereomers. LCMS (M+H)=633.5

Example 19 and 20

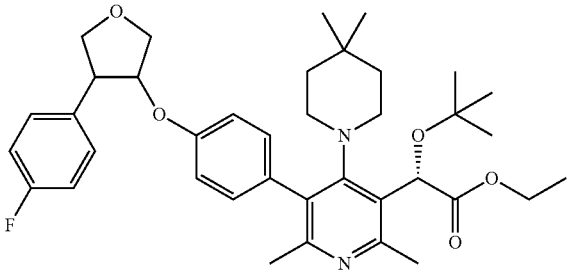 [SMILES: CCOC(=O)[C@@H](OC(C)(C)C)c1c(C)nc(C)c(-c2ccc(OC3COCC3c3ccc(F)cc3)cc2)c1N1CCC(C)(C)CC1]

Example 19

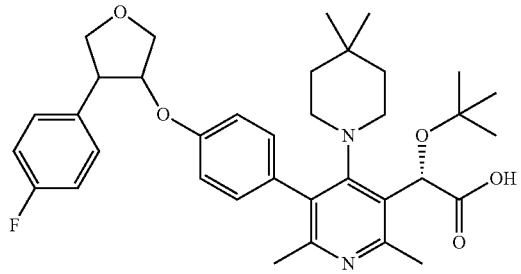

Example 20

(2S)-2-(tert-Butoxy)-2-(4-(4,4-dimethylpiperidin-1-yl)-5-(4-((4-(4-fluorophenyl)tetrahydrofuran-3-yl)oxy)phenyl)-2,6-dimethylpyridin-3-yl)acetic Acid To a solution of (2S)-ethyl 2-(tert-butoxy)-2-(4-(4,4-dimethylpiperidin-1-yl)-5-(4-((4-(4-fluorophenyl)tetrahydrofuran-3-yl)oxy)phenyl)-2,6-dimethylpyridin-3-yl)acetate (120 mg, 0.190 mmol) in ethanol (3 mL) was added 1N NaOH (0.948 mL, 0.948 mmol) and the resulting mixture was heated at 80° C. for 5 h. Mixture was then cooled and purified by chiral SFC to afford two diastereomers.

Example 19: First Eluting Diastereomer (2S)-2-(tert-Butoxy)-2-(4-(4,4-dimethylpiperidin-1-yl)-5-(4-((4-(4-fluorophenyl)tetrahydrofuran-3-yl)oxy)phenyl)-2,6-dimethylpyridin-3-yl)acetic acid (23.3 mg, 0.039 mmol, 20.32% yield). $^1$H NMR (500 MHz, DMSO-d$_6$) δ 7.42 (t, J=7.0 Hz, 2H), 7.14-7.03 (m, 3H), 7.00-6.87 (m, 2H), 6.83 (d, J=8.1 Hz, 1H), 5.80 (br. s., 1H), 5.20 (br. s., 1H), 4.26-4.18 (m, 2H), 4.06 (t, J=9.2 Hz, 1H), 3.92 (d, J=9.5 Hz, 1H), 3.73 (br. s., 1H), 3.26 (br. s., 1H), 2.78 (br. s., 1H), 2.42 (s, 3H), 2.10 (d, J=11.0 Hz, 1H), 2.01 (s, 3H), 1.80 (t, J=10.6 Hz, 1H), 1.47 (br. s., 1H), 1.25 (d, J=16.1 Hz, 1H), 1.16 (d, J=12.5 Hz, 1H), 1.11 (s, 9H), 1.00 (d, J=12.1 Hz, 1H), 0.85 (br. s., 3H), 0.58 (br. s., 3H). LCMS (M+H)=605.1.

Example 20: Second Eluting Diasteromer (2S)-2-(tert-Butoxy)-2-(4-(4,4-dimethylpiperidin-1-yl)-5-(4-((4-(4-fluorophenyl)tetrahydrofuran-3-yl)oxy)phenyl)-2,6-dimethylpyridin-3-yl)acetic acid (24.4 mg, 0.040 mmol, 21.28% yield). $^1$H NMR (500 MHz, DMSO-d$_6$) δ 7.44-7.36 (m, 2H), 7.16-7.04 (m, 3H), 7.00-6.92 (m, 1H), 6.87 (d, J=8.4 Hz, 2H), 5.85 (br. s., 1H), 5.20 (br. s., 1H), 4.27-4.16 (m, 2H), 4.07 (t, J=9.0 Hz, 1H), 3.99-3.87 (m, 1H), 3.79-3.66 (m, 1H), 3.18 (d, J=5.1 Hz, 1H), 2.77 (br. s., 1H), 2.43

(s, 3H), 2.16 (d, J=11.0 Hz, 1H), 1.99 (s, 3H), 1.95-1.86 (m, 1H), 1.47 (br. s., 1H), 1.26 (d, J=19.4 Hz, 1H), 1.16 (d, J=11.4 Hz, 1H), 1.12 (s, 9H), 1.01 (d, J=13.9 Hz, 1H), 0.85 (br. s., 3H), 0.58 (br. s., 3H). LCMS (M+H)=605.1.

Biological Methods

Inhibition of HIV Replication:

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where (Fa)=1/[1+ ($ED_{50}$/drug conc.)$^m$] (Johnson V A, Byington R T. Infectivity Assay. In *Techniques in HIV Research*. ed. Aldovini A, Walker B D. 71-76. New York: Stockton Press. 1990). Results are shown in Table 1. Activity equal to A refers to a compound having an $EC_{50} \leq 100$ nM, while B and C denote compounds having an $EC_{50}$ between 100 nM and 1 uM (B) or >1 uM (C).

TABLE 1

| Example | Activity | $EC_{50}$ μM |
|---|---|---|
| 1 | B | 0.117 |
| 2 | A | 0.034 |
| 3 | A | |
| 4 | A | |
| 5 | A | 0.021 |
| 6 | A | |
| 7 | A | |
| 8 | A | |
| 9 | A | |
| 10 | A | |
| 11 | A | 0.003 |
| 12 | A | |
| 13 | A | 0.003 |
| 14 | A | |
| 15 | A | |
| 16 | A | |
| 17 | A | 0.012 |
| 18 | A | |
| 19 | A | |
| 20 | A | |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I or a pharmaceutically acceptable salt thereof

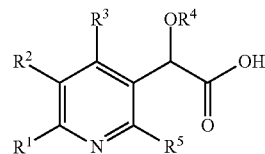

wherein:
$R^1$ is selected from hydrogen or alkyl;
$R^2$ is selected from $(R^6O)$phenyl or $(R^8O)$phenyl;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, or haloalkoxy;
$R^4$ is selected from alkyl or haloalkyl;
$R^5$ is alkyl;
$R^6$ is $((R^9)(R^{10})N)C_{2-5}$alkyl;
$R^7$ is selected from alkyl, (cycloalkyl)alkyl, ((alkyl)cycloalkyl)alkyl, cycloalkyl, (alkyl)cycloalkyl, or tetrahydropyranyl, and is further substituted with 0-1 $Ar^1$ substituents;
$R^8$ is selected from indanyl or chromanyl;
$R^9$ is selected from hydrogen or alkyl;
$R^{10}$ is selected from hydrogen or alkyl; or $R^9$ and $R^{10}$ taken together is selected from azetidinyl, pyrrolidinyl, piperidinyl, piperazinyl, morpholinyl, thiomorpholinyl, 1,1-dioxidethiomorpholinyl, homopiperidinyl, homopiperazinyl, or homomorpholinyl, and is substituted with 0-2 alkyl substituents and with 0-1 $Ar^1$ or 0-1 $(Ar^1)C_{1-3}$-alkyl substituents; and
$Ar^1$ is phenyl substituted with 0-3 substituents selected from halo, alkyl, haloalkyl, alkoxy, and haloalkoxy.

2. A compound or salt of claim 1 wherein:
$R^1$ is alkyl; and
$R^3$ is piperidinyl substituted with 0-3 substituents selected from cyano, halo, alkyl, haloalkyl, alkoxy, or haloalkoxy.

3. A compound or salt of claim 1 wherein;
$R^2$ is $(R^6O)$phenyl; and
$R^3$ is piperidinyl substituted with 0-3 substituents selected from cyano, halo, alkyl, haloalkyl, alkoxy, or haloalkoxy.

4. A compound or salt of claim 1 wherein;
$R^1$ is alkyl;
$R^2$ is $(R^8O)$phenyl; and
$R^3$ is piperidinyl substituted with 0-3 substituents selected from cyano, halo, alkyl, haloalkyl, alkoxy, or haloalkoxy.

5. A compound or salt of claim 1 wherein $R^3$ is piperidinyl substituted with 0-3 substituents selected from cyano, halo, alkyl, haloalkyl, alkoxy, or haloalkoxy.

6. A compound of Formula I or a pharmaceutically acceptable salt thereof

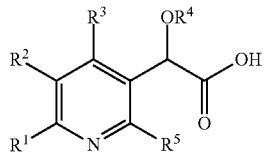

wherein:
$R^1$ is alkyl;
$R^2$ is selected from $(R^6O)$phenyl or $(R^8O)$phenyl;
$R^3$ is piperidinyl substituted with 0-3 substituents selected from cyano, halo, alkyl, haloalkyl, alkoxy, or haloalkoxy;
$R^4$ is selected from alkyl or haloalkyl;
$R^5$ is alkyl;
$R^6$ is $((R^9)(R^{10})N)C_{2-5}$alkyl;
$R^7$ is selected from alkyl, (cycloalkyl)alkyl, ((alkyl)cycloalkyl)alkyl, cycloalkyl, (alkyl)cycloalkyl, or tetrahydropyranyl, and is further substituted with 0-1 $Ar^1$ substituents;
$R^8$ is selected from indanyl or chromanyl;
$R^9$ is selected from hydrogen or alkyl; and
$R^{10}$ is selected from hydrogen or alkyl.

7. A compound or salt of claim 6 wherein $R^2$ is $(R^6O)$ phenyl.

8. A compound or salt of claim 6 wherein $R^2$ is $(R^8O)$ phenyl.

9. A composition useful for treating HIV infection comprising a compound or salt of claim 1 and a pharmaceutically acceptable carrier.

10. The composition of claim 9 further comprising at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

11. The composition of claim 10 wherein the other agent is dolutegravir.

12. A method for treating HIV infection comprising administering a compound of claim 1, or a pharmaceutically acceptable salt thereof, to a patient in need thereof.

13. The method of claim 12 further comprising administering at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

14. The method of claim 13 wherein the other agent is dolutegravir.

15. The method of claim 14 wherein the other agent is administered to the patient prior to, simultaneously with, or subsequently to the compound of claim 1.

* * * * *